(12) United States Patent
Long et al.

(10) Patent No.: US 10,004,558 B2
(45) Date of Patent: Jun. 26, 2018

(54) ELECTRICAL ABLATION DEVICES

(71) Applicant: Ethicon Endo-Surgery, Inc., Cincinnati, OH (US)

(72) Inventors: Gary L. Long, Cincinnati, OH (US); Ragae M. Ghabrial, Pittsburgh, PA (US); David N. Plescia, Mentor, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 524 days.

(21) Appl. No.: 14/673,111

(22) Filed: Mar. 30, 2015

(65) Prior Publication Data
US 2015/0265342 A1 Sep. 24, 2015

Related U.S. Application Data

(60) Continuation of application No. 13/602,742, filed on Sep. 4, 2012, now Pat. No. 9,011,431, which is a
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 18/1477* (2013.01);
(Continued)

(58) Field of Classification Search
CPC .............. A61M 25/10; A61M 25/1043; A61M 25/1084
See application file for complete search history.

(56) References Cited

U.S. PATENT DOCUMENTS 645,576 A 3/1900 Telsa
649,621 A 5/1900 Tesla
(Continued)

FOREIGN PATENT DOCUMENTS

AU 666310 B2 2/1996
DE 3008120 A1 9/1980
(Continued)

OTHER PUBLICATIONS

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
(Continued)

*Primary Examiner* — Laura Bouchelle

(57) ABSTRACT

An electrical ablation apparatus comprises first and second electrodes. Each electrode comprises a first end configured to couple an energy source and a second end configured to couple to a tissue treatment region. An energy source is coupled to the first and second electrodes. The energy source is configured to deliver a first series of electrical pulses sufficient to induce cell necrosis by irreversible electroporation and a second series of electrical pulses sufficient to induce cell necrosis by thermal heating, through at least one of the first and second electrodes. The first series of electrical pulses is characterized by a first amplitude, a first pulse length, and a first frequency. The second series of electrical pulses is characterized by a second amplitude, a second pulse length, and a second frequency.

13 Claims, 16 Drawing Sheets

Related U.S. Application Data division of application No. 12/352,375, filed on Jan. 12, 2009, now Pat. No. 8,361,066.

(52) U.S. Cl.
CPC ............... *A61B 2018/00214* (2013.01); *A61B 2018/00482* (2013.01); *A61B 2018/00547* (2013.01); *A61B 2018/00577* (2013.01); *A61B 2018/00613* (2013.01); *A61B 2018/00898* (2013.01); *A61B 2018/124* (2013.01); *A61B 2018/1425* (2013.01)

(56) References Cited

U.S. PATENT DOCUMENTS

| | | | |
|---|---|---|---|
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould |
| 1,916,722 A | 7/1933 | Ende |
| 2,028,635 A | 1/1936 | Wappler |
| 2,031,682 A | 2/1936 | Wappler |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A | 10/1948 | Emsig |
| 2,493,108 A | 1/1950 | Casey |
| 2,504,152 A | 4/1950 | Riker |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gattuma et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |

(56) References Cited

U.S. PATENT DOCUMENTS

| | | |
|---|---|---|
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |

(56) References Cited

U.S. PATENT DOCUMENTS

| | | |
|---|---|---|
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |

(56) References Cited

U.S. PATENT DOCUMENTS

| | | |
|---|---|---|
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Lepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A * | 9/2000 | Tu .................... A61B 18/1492 606/41 |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |

(56) References Cited

U.S. PATENT DOCUMENTS

| | | | |
|---|---|---|---|
| 6,277,136 | B1 | 8/2001 | Bonutti |
| 6,283,963 | B1 | 9/2001 | Regula |
| 6,287,304 | B1 | 9/2001 | Eggers et al. |
| 6,293,909 | B1 | 9/2001 | Chu et al. |
| 6,293,952 | B1 | 9/2001 | Brosens et al. |
| 6,296,630 | B1 | 10/2001 | Altman et al. |
| 6,314,963 | B1 | 11/2001 | Vaska et al. |
| 6,322,578 | B1 | 11/2001 | Houle et al. |
| 6,325,534 | B1 | 12/2001 | Hawley et al. |
| 6,326,177 | B1 | 12/2001 | Schoenbach et al. |
| 6,328,730 | B1 | 12/2001 | Harkrider, Jr. |
| 6,350,267 | B1 | 2/2002 | Stefanchik |
| 6,350,278 | B1 | 2/2002 | Lenker et al. |
| 6,352,503 | B1 | 3/2002 | Matsui et al. |
| 6,352,541 | B1 | 3/2002 | Kienzle et al. |
| 6,352,543 | B1 | 3/2002 | Cole |
| 6,355,013 | B1 | 3/2002 | van Muiden |
| 6,355,035 | B1 | 3/2002 | Manushakian |
| 6,361,534 | B1 | 3/2002 | Chen et al. |
| 6,364,879 | B1 | 4/2002 | Chen et al. |
| 6,368,340 | B2 | 4/2002 | Malecki et al. |
| 6,371,956 | B1 | 4/2002 | Wilson et al. |
| 6,379,366 | B1 | 4/2002 | Fleischman et al. |
| 6,383,195 | B1 | 5/2002 | Richard |
| 6,383,197 | B1 | 5/2002 | Conlon et al. |
| 6,387,671 | B1 | 5/2002 | Rubinsky et al. |
| 6,391,029 | B1 | 5/2002 | Hooven et al. |
| 6,398,708 | B1 | 6/2002 | Hastings et al. |
| 6,402,735 | B1 | 6/2002 | Langevin |
| 6,402,746 | B1 | 6/2002 | Whayne et al. |
| 6,406,440 | B1 | 6/2002 | Stefanchik |
| 6,409,727 | B1 | 6/2002 | Bales et al. |
| 6,409,733 | B1 | 6/2002 | Conlon et al. |
| 6,419,639 | B2 | 7/2002 | Walther et al. |
| 6,419,641 | B1 | 7/2002 | Mark et al. |
| 6,427,089 | B1 | 7/2002 | Knowlton |
| 6,431,500 | B1 | 8/2002 | Jacobs et al. |
| 6,436,107 | B1 | 8/2002 | Wang et al. |
| 6,443,970 | B1 | 9/2002 | Schulze et al. |
| 6,443,988 | B2 | 9/2002 | Felt et al. |
| 6,447,444 | B1 | 9/2002 | Avni et al. |
| 6,447,511 | B1 | 9/2002 | Slater |
| 6,447,523 | B1 | 9/2002 | Middleman et al. |
| 6,454,783 | B1 | 9/2002 | Piskun |
| 6,454,785 | B2 | 9/2002 | De Hoyos Garza |
| 6,458,074 | B1 | 10/2002 | Matsui et al. |
| 6,458,076 | B1 | 10/2002 | Pruitt |
| 6,464,701 | B1 | 10/2002 | Hooven et al. |
| 6,464,702 | B2 | 10/2002 | Schulze et al. |
| 6,470,218 | B1 | 10/2002 | Behl |
| 6,475,104 | B1 | 11/2002 | Lutz et al. |
| 6,485,411 | B1 | 11/2002 | Konstorum et al. |
| 6,489,745 | B1 | 12/2002 | Koreis |
| 6,491,626 | B1 | 12/2002 | Stone et al. |
| 6,491,627 | B1 | 12/2002 | Komi |
| 6,491,691 | B1 | 12/2002 | Morley et al. |
| 6,493,590 | B1 | 12/2002 | Wessman et al. |
| 6,494,893 | B2 | 12/2002 | Dubrul et al. |
| 6,500,176 | B1 | 12/2002 | Truckai et al. |
| 6,503,192 | B1 | 1/2003 | Ouchi |
| 6,506,190 | B1 | 1/2003 | Walshe |
| 6,508,827 | B1 | 1/2003 | Manhes |
| 6,514,239 | B2 | 2/2003 | Shimmura et al. |
| 6,517,534 | B1 | 2/2003 | McGovern et al. |
| 6,520,954 | B2 | 2/2003 | Ouchi |
| 6,526,320 | B2 | 2/2003 | Mitchell |
| 6,527,782 | B2 | 3/2003 | Hogg et al. |
| 6,530,880 | B2 | 3/2003 | Pagliuca |
| 6,530,922 | B2 | 3/2003 | Cosman et al. |
| 6,535,764 | B2 | 3/2003 | Imran et al. |
| 6,537,200 | B2 | 3/2003 | Leysieffer et al. |
| 6,543,456 | B1 | 4/2003 | Freeman |
| 6,551,270 | B1 | 4/2003 | Bimbo et al. |
| 6,551,356 | B2 | 4/2003 | Rousseau |
| 6,554,766 | B2 | 4/2003 | Maeda et al. |
| 6,554,823 | B2 | 4/2003 | Palmer et al. |
| 6,554,829 | B2 | 4/2003 | Schulze et al. |
| 6,558,384 | B2 | 5/2003 | Mayenberger |
| 6,562,034 | B2 | 5/2003 | Edwards et al. |
| 6,562,035 | B1 | 5/2003 | Levin |
| 6,562,052 | B2 | 5/2003 | Nobles et al. |
| 6,569,085 | B2 | 5/2003 | Kortenbach et al. |
| 6,569,091 | B2 | 5/2003 | Diokno et al. |
| 6,569,120 | B1 | 5/2003 | Green et al. |
| 6,569,159 | B1 | 5/2003 | Edwards et al. |
| 6,572,629 | B2 | 6/2003 | Kalloo et al. |
| 6,572,635 | B1 | 6/2003 | Bonutti |
| 6,575,988 | B2 | 6/2003 | Rousseau |
| 6,579,311 | B1 | 6/2003 | Makower |
| 6,581,889 | B2 | 6/2003 | Carpenter et al. |
| 6,585,642 | B2 | 7/2003 | Christopher |
| 6,585,717 | B1 | 7/2003 | Wittenberger et al. |
| 6,587,750 | B2 | 7/2003 | Gerbi et al. |
| 6,592,559 | B1 | 7/2003 | Pakter et al. |
| 6,592,603 | B2 | 7/2003 | Lasner |
| 6,594,971 | B1 | 7/2003 | Addy et al. |
| 6,602,262 | B2 | 8/2003 | Griego et al. |
| 6,605,105 | B1 | 8/2003 | Cuschieri et al. |
| 6,610,072 | B1 | 8/2003 | Christy et al. |
| 6,610,074 | B2 | 8/2003 | Santilli |
| 6,613,038 | B2 | 9/2003 | Bonutti et al. |
| 6,613,068 | B2 | 9/2003 | Ouchi |
| 6,616,632 | B2 | 9/2003 | Sharp et al. |
| 6,620,193 | B1 | 9/2003 | Lau et al. |
| 6,623,448 | B2 | 9/2003 | Slater |
| 6,626,919 | B1 | 9/2003 | Swanstrom |
| 6,632,171 | B2 | 10/2003 | Iddan et al. |
| 6,632,229 | B1 | 10/2003 | Yamanouchi |
| 6,632,234 | B2 | 10/2003 | Kieturakis et al. |
| 6,638,275 | B1 | 10/2003 | McGaffigan et al. |
| 6,638,286 | B1 | 10/2003 | Burbank et al. |
| 6,645,225 | B1 | 11/2003 | Atkinson |
| 6,652,518 | B2 | 11/2003 | Wellman et al. |
| 6,652,521 | B2 | 11/2003 | Schulze |
| 6,652,545 | B2 | 11/2003 | Shipp et al. |
| 6,652,551 | B1 | 11/2003 | Heiss |
| 6,656,194 | B1 | 12/2003 | Gannoe et al. |
| 6,663,641 | B1 | 12/2003 | Kovac et al. |
| 6,663,655 | B2 | 12/2003 | Ginn et al. |
| 6,666,854 | B1 | 12/2003 | Lange |
| 6,672,338 | B1 | 1/2004 | Esashi et al. |
| 6,673,058 | B2 | 1/2004 | Snow |
| 6,673,070 | B2 | 1/2004 | Edwards et al. |
| 6,673,087 | B1 | 1/2004 | Chang et al. |
| 6,673,092 | B1 | 1/2004 | Bacher |
| 6,676,685 | B2 | 1/2004 | Pedros et al. |
| 6,679,882 | B1 | 1/2004 | Kornerup |
| 6,685,628 | B2 | 2/2004 | Vu |
| 6,685,724 | B1 | 2/2004 | Haluck |
| 6,692,445 | B2 | 2/2004 | Roberts et al. |
| 6,692,462 | B2 | 2/2004 | Mackenzie et al. |
| 6,692,493 | B2 | 2/2004 | McGovern et al. |
| 6,699,180 | B2 | 3/2004 | Kobayashi |
| 6,699,256 | B1 | 3/2004 | Logan et al. |
| 6,699,263 | B2 | 3/2004 | Cope |
| 6,706,018 | B2 | 3/2004 | Westlund et al. |
| 6,708,066 | B2 | 3/2004 | Herbst et al. |
| 6,709,188 | B2 | 3/2004 | Ushimaru |
| 6,709,445 | B2 | 3/2004 | Boebel et al. |
| 6,716,226 | B2 | 4/2004 | Sixto, Jr. et al. |
| 6,731,875 | B1 | 5/2004 | Kartalopoulos |
| 6,736,822 | B2 | 5/2004 | McClellan et al. |
| 6,740,030 | B2 | 5/2004 | Martone et al. |
| 6,740,082 | B2 | 5/2004 | Shadduck |
| 6,743,166 | B2 | 6/2004 | Berci et al. |
| 6,743,226 | B2 | 6/2004 | Cosman et al. |
| 6,743,239 | B1 | 6/2004 | Kuehn et al. |
| 6,743,240 | B2 | 6/2004 | Smith et al. |
| 6,749,560 | B1 | 6/2004 | Konstorum et al. |
| 6,749,609 | B1 | 6/2004 | Lunsford et al. |
| 6,752,768 | B2 | 6/2004 | Burdorff et al. |
| 6,752,811 | B2 | 6/2004 | Chu et al. |
| 6,752,822 | B2 | 6/2004 | Jespersen |
| 6,758,857 | B2 | 7/2004 | Cioanta et al. |

(56) References Cited

U.S. PATENT DOCUMENTS

| | | |
|---|---|---|
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,814,697 B2 | 11/2004 | Ouchi |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,852,078 B2 | 2/2005 | Ouchi |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,869,395 B2 | 3/2005 | Page et al. |
| 6,869,398 B2 | 3/2005 | Obenchain et al. |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,911,019 B2 | 6/2005 | Mulier et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,858 B2 | 12/2005 | Fuimaono et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |

(56) References Cited

U.S. PATENT DOCUMENTS

| | | |
|---|---|---|
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,169,115 B2 | 1/2007 | Nobis et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,189,231 B2 | 3/2007 | Clague et al. |
| 7,195,612 B2 | 3/2007 | van Sloten et al. |
| 7,195,631 B2 | 3/2007 | Dumbauld |
| 7,204,804 B2 | 4/2007 | Zirps et al. |
| 7,204,820 B2 | 4/2007 | Akahoshi |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francese et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,241,295 B2 | 7/2007 | Maguire et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,261,728 B2 | 8/2007 | Long et al. |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,331,968 B2 | 2/2008 | Arp et al. |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,352,387 B2 | 4/2008 | Yamamoto |
| 7,357,806 B2 | 4/2008 | Rivera et al. |
| 7,364,582 B2 | 4/2008 | Lee |
| 7,367,939 B2 | 5/2008 | Smith et al. |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,431,694 B2 | 10/2008 | Stefanchik et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,520,950 B2 | 4/2009 | Saadat et al. |
| 7,524,281 B2 | 4/2009 | Chu et al. |
| 7,524,302 B2 | 4/2009 | Tower |
| 7,534,228 B2 | 5/2009 | Williams |
| 7,536,217 B2 | 5/2009 | Minai et al. |
| 7,540,872 B2 | 6/2009 | Schechter et al. |
| 7,542,807 B2 | 6/2009 | Bertolero et al. |
| 7,544,195 B2 | 6/2009 | Lunsford et al. |
| 7,544,203 B2 | 6/2009 | Chin et al. |
| 7,547,310 B2 | 6/2009 | Whitfield |
| 7,548,040 B2 | 6/2009 | Lee et al. |
| 7,549,564 B2 | 6/2009 | Boudreaux |
| 7,549,990 B2 | 6/2009 | Canady |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,300 B2 | 7/2009 | Devierre et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,578,832 B2 | 8/2009 | Johnson et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,591,783 B2 | 9/2009 | Boulais et al. |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,615,002 B2 | 11/2009 | Rothweiler et al. |
| 7,615,003 B2 | 11/2009 | Stefanchik et al. |
| 7,615,005 B2 | 11/2009 | Stefanchik et al. |
| 7,615,058 B2 | 11/2009 | Sixto, Jr. et al. |
| 7,615,067 B2 | 11/2009 | Lee et al. |
| 7,618,398 B2 | 11/2009 | Holman et al. |
| 7,618,437 B2 | 11/2009 | Nakao |
| 7,621,927 B2 | 11/2009 | Messerly et al. |
| 7,621,936 B2 | 11/2009 | Cragg et al. |

(56) References Cited

U.S. PATENT DOCUMENTS

| | | |
|---|---|---|
| 7,628,792 B2 | 12/2009 | Guerra |
| 7,628,797 B2 | 12/2009 | Tieu et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,637,905 B2 | 12/2009 | Saadat et al. |
| 7,645,288 B2 | 1/2010 | McKenna et al. |
| 7,648,457 B2 | 1/2010 | Stefanchik et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,658,738 B2 | 2/2010 | Nobis et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,670,346 B2 | 3/2010 | Whitfield |
| 7,674,259 B2 | 3/2010 | Shadduck |
| 7,674,275 B2 | 3/2010 | Martin et al. |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,691,103 B2 | 4/2010 | Fernandez et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,708,756 B2 | 5/2010 | Nobis et al. |
| 7,713,189 B2 | 5/2010 | Hanke |
| 7,713,270 B2 | 5/2010 | Suzuki |
| 7,721,742 B2 | 5/2010 | Kalloo et al. |
| 7,727,242 B2 | 6/2010 | Sepetka et al. |
| 7,727,246 B2 | 6/2010 | Sixto, Jr. et al. |
| 7,727,248 B2 | 6/2010 | Smith et al. |
| 7,727,249 B2 | 6/2010 | Rahmani |
| 7,731,725 B2 | 6/2010 | Gadberry et al. |
| 7,736,374 B2 | 6/2010 | Vaughan et al. |
| 7,744,591 B2 | 6/2010 | Rioux et al. |
| 7,744,615 B2 | 6/2010 | Couture |
| 7,749,161 B2 | 7/2010 | Beckman et al. |
| 7,749,163 B2 | 7/2010 | Mulac et al. |
| 7,751,866 B2 | 7/2010 | Aoki et al. |
| 7,751,869 B2 | 7/2010 | Rioux et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,758,598 B2 | 7/2010 | Conlon et al. |
| 7,762,949 B2 | 7/2010 | Nakao |
| 7,762,959 B2 | 7/2010 | Bilsbury |
| 7,762,960 B2 | 7/2010 | Timberlake et al. |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,896 B2 | 8/2010 | Komkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,639 B2 | 8/2010 | Van Lue |
| 7,780,683 B2 | 8/2010 | Roue et al. |
| 7,780,691 B2 | 8/2010 | Stefanchik |
| 7,784,663 B2 | 8/2010 | Shelton, IV |
| 7,785,348 B2 | 8/2010 | Kuhns et al. |
| 7,789,825 B2 | 9/2010 | Nobis et al. |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,798,960 B2 | 9/2010 | Jaeger |
| 7,813,590 B2 | 10/2010 | Horn et al. |
| 7,813,789 B2 | 10/2010 | Glukhovsky |
| 7,815,565 B2 | 10/2010 | Stefanchik et al. |
| 7,815,566 B2 | 10/2010 | Stefanchik et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,828,808 B2 | 11/2010 | Hinman et al. |
| 7,833,156 B2 | 11/2010 | Williams et al. |
| 7,833,238 B2 | 11/2010 | Nakao |
| 7,837,615 B2 | 11/2010 | Le et al. |
| 7,842,028 B2 | 11/2010 | Lee |
| 7,842,050 B2 | 11/2010 | Diduch et al. |
| 7,842,068 B2 | 11/2010 | Ginn |
| 7,846,087 B2 | 12/2010 | Stefanchik et al. |
| 7,846,107 B2 | 12/2010 | Hoffman et al. |
| 7,846,171 B2 | 12/2010 | Kullas et al. |
| 7,850,660 B2 | 12/2010 | Uth et al. |
| 7,850,686 B2 | 12/2010 | Nobis et al. |
| 7,850,712 B2 | 12/2010 | Conlon et al. |
| 7,857,183 B2 | 12/2010 | Shelton, IV |
| 7,862,546 B2 | 1/2011 | Conlon et al. |
| 7,862,553 B2 | 1/2011 | Ewaschuk |
| 7,862,572 B2 | 1/2011 | Meade et al. |
| 7,862,582 B2 | 1/2011 | Ortiz et al. |
| 7,867,216 B2 | 1/2011 | Wahr et al. |
| 7,871,371 B2 | 1/2011 | Komiya et al. |
| 7,875,042 B2 | 1/2011 | Martin et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,905,830 B2 | 3/2011 | Stefanchik et al. |
| 7,909,809 B2 | 3/2011 | Scopton et al. |
| 7,914,513 B2 | 3/2011 | Voorhees, Jr. |
| 7,918,783 B2 | 4/2011 | Maseda et al. |
| 7,918,785 B2 | 4/2011 | Okada et al. |
| 7,918,844 B2 | 4/2011 | Byrum et al. |
| 7,918,845 B2 | 4/2011 | Saadat et al. |
| 7,918,848 B2 | 4/2011 | Lau et al. |
| 7,918,869 B2 | 4/2011 | Saadat et al. |
| 7,922,650 B2 | 4/2011 | McWeeney et al. |
| 7,922,717 B2 | 4/2011 | Sugita |
| 7,922,739 B2 | 4/2011 | Downey |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,931,661 B2 | 4/2011 | Saadat et al. |
| 7,935,130 B2 | 5/2011 | Williams |
| 7,937,143 B2 | 5/2011 | Demarais et al. |
| 7,945,332 B2 | 5/2011 | Schechter |
| 7,947,000 B2 | 5/2011 | Vargas et al. |
| 7,951,073 B2 | 5/2011 | Freed |
| 7,953,326 B2 | 5/2011 | Farr et al. |
| 7,955,298 B2 | 6/2011 | Carroll et al. |
| 7,955,340 B2 | 6/2011 | Michlitsch et al. |
| 7,955,355 B2 | 6/2011 | Chin |
| 7,959,627 B2 | 6/2011 | Utley et al. |
| 7,959,629 B2 | 6/2011 | Young et al. |
| 7,959,642 B2 | 6/2011 | Nobis et al. |
| 7,963,192 B2 | 6/2011 | Mayenberger et al. |
| 7,963,912 B2 | 6/2011 | Zwolinski et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,967,842 B2 | 6/2011 | Bakos |
| 7,969,473 B2 | 6/2011 | Kotoda |
| 7,972,330 B2 | 7/2011 | Alejandro et al. |
| 7,972,333 B2 | 7/2011 | Nishimura |
| 7,976,458 B2 | 7/2011 | Stefanchik et al. |
| 7,976,552 B2 | 7/2011 | Suzuki |
| 7,985,239 B2 | 7/2011 | Suzuki |
| 7,988,618 B2 | 8/2011 | Mikkaichi et al. |

(56) References Cited

U.S. PATENT DOCUMENTS

| | | |
|---|---|---|
| 7,988,685 B2 | 8/2011 | Ziaie et al. |
| 7,988,690 B2 | 8/2011 | Chanduszko et al. |
| 7,998,132 B2 | 8/2011 | Gregorich et al. |
| 8,007,474 B2 | 8/2011 | Uth et al. |
| 8,021,358 B2 | 9/2011 | Doyle et al. |
| 8,021,362 B2 | 9/2011 | Deem et al. |
| 8,021,378 B2 | 9/2011 | Sixto, Jr. et al. |
| 8,029,504 B2 | 10/2011 | Long |
| 8,034,046 B2 | 10/2011 | Eidenschink |
| 8,037,591 B2 | 10/2011 | Spivey et al. |
| 8,038,596 B2 | 10/2011 | Miyake et al. |
| 8,038,612 B2 | 10/2011 | Paz |
| 8,043,289 B2 | 10/2011 | Behl et al. |
| 8,048,060 B2 | 11/2011 | Griffin et al. |
| 8,048,067 B2 | 11/2011 | Davalos et al. |
| 8,048,108 B2 | 11/2011 | Sibbitt, Jr. et al. |
| 8,052,597 B2 | 11/2011 | Boulais |
| 8,052,699 B1 | 11/2011 | Sherwinter |
| 8,057,462 B2 | 11/2011 | Weitzner et al. |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, III et al. |
| 8,070,743 B2 | 12/2011 | Kagan et al. |
| 8,070,759 B2 | 12/2011 | Stefanchik et al. |
| 8,070,804 B2 | 12/2011 | Hyde et al. |
| 8,075,478 B2 | 12/2011 | Campos |
| 8,075,567 B2 | 12/2011 | Taylor et al. |
| 8,075,572 B2 | 12/2011 | Stefanchik et al. |
| 8,075,573 B2 | 12/2011 | Gambale et al. |
| 8,075,587 B2 | 12/2011 | Ginn |
| 8,088,062 B2 | 1/2012 | Zwolinski |
| 8,092,374 B2 | 1/2012 | Smith et al. |
| 8,092,549 B2 | 1/2012 | Hillis et al. |
| 8,096,459 B2 | 1/2012 | Ortiz et al. |
| 8,096,941 B2 | 1/2012 | Fowler et al. |
| 8,096,998 B2 | 1/2012 | Cresina |
| 8,097,001 B2 | 1/2012 | Nakao |
| 8,100,922 B2 | 1/2012 | Griffith |
| 8,109,872 B2 | 2/2012 | Kennedy, II et al. |
| 8,109,919 B2 | 2/2012 | Kraft et al. |
| 8,109,926 B2 | 2/2012 | Azure |
| 8,114,072 B2 | 2/2012 | Long et al. |
| 8,114,113 B2 | 2/2012 | Becker |
| 8,114,119 B2 | 2/2012 | Spivey et al. |
| 8,118,738 B2 | 2/2012 | Larkin |
| 8,118,821 B2 | 2/2012 | Mouw |
| 8,118,834 B1 | 2/2012 | Goraltchouk et al. |
| 8,118,835 B2 | 2/2012 | Weisel et al. |
| 8,123,677 B2 | 2/2012 | Fujimori |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,817 B2 | 4/2012 | Bonadio et al. |
| 8,157,834 B2 | 4/2012 | Conlon |
| 8,159,549 B2 | 4/2012 | Glukhovsky et al. |
| 8,167,894 B2 | 5/2012 | Miles et al. |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,200,334 B1 | 6/2012 | Min et al. |
| 8,202,265 B2 | 6/2012 | Boulais |
| 8,202,295 B2 | 6/2012 | Kaplan |
| 8,206,295 B2 | 6/2012 | Kaul |
| 8,211,119 B2 | 7/2012 | Palmer et al. |
| 8,211,125 B2 | 7/2012 | Spivey |
| 8,216,224 B2 | 7/2012 | Morris et al. |
| 8,216,252 B2 | 7/2012 | Vaughan et al. |
| 8,216,255 B2 | 7/2012 | Smith et al. |
| 8,221,310 B2 | 7/2012 | Saadat et al. |
| 8,221,411 B2 | 7/2012 | Francischelli et al. |
| 8,241,204 B2 | 8/2012 | Spivey |
| 8,241,309 B2 | 8/2012 | Miles et al. |
| 8,246,633 B2 | 8/2012 | Omori |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |
| 8,267,854 B2 | 9/2012 | Asada et al. |
| 8,277,373 B2 | 10/2012 | Maahs et al. |
| 8,282,665 B2 | 10/2012 | Kieturakis et al. |
| 8,298,161 B2 | 10/2012 | Vargas |
| 8,303,581 B2 | 11/2012 | Arts et al. |
| 8,308,682 B2 | 11/2012 | Kramer et al. |
| 8,308,738 B2 | 11/2012 | Nobis et al. |
| 8,308,743 B2 | 11/2012 | Matsuno et al. |
| 8,313,496 B2 | 11/2012 | Sauer et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,333,691 B2 | 12/2012 | Schaaf |
| 8,333,777 B2 | 12/2012 | Schaller et al. |
| 8,337,394 B2 | 12/2012 | Vakharia |
| 8,337,492 B2 | 12/2012 | Kunis et al. |
| 8,337,510 B2 | 12/2012 | Rieber et al. |
| 8,343,041 B2 | 1/2013 | Byers et al. |
| 8,348,827 B2 | 1/2013 | Zwolinski |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,366,606 B2 | 2/2013 | Watanabe et al. |
| 8,377,044 B2 | 2/2013 | Coe et al. |
| 8,377,057 B2 | 2/2013 | Rick et al. |
| 8,382,790 B2 | 2/2013 | Uenohara et al. |
| 8,388,653 B2 | 3/2013 | Nobis et al. |
| 8,394,090 B2 | 3/2013 | Ootsubo |
| 8,403,926 B2 | 3/2013 | Nobis et al. |
| 8,409,076 B2 | 4/2013 | Pang et al. |
| 8,409,197 B2 | 4/2013 | Slater |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,460,275 B2 | 6/2013 | Taylor et al. |
| 8,465,419 B2 | 6/2013 | Moriyama |
| 8,465,484 B2 | 6/2013 | Davalos et al. |
| 8,469,993 B2 | 6/2013 | Rothberg et al. |
| 8,475,359 B2 | 7/2013 | Asada et al. |
| 8,475,361 B2 | 7/2013 | Barlow et al. |
| 8,475,452 B2 | 7/2013 | Van Wyk et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,517,921 B2 | 8/2013 | Tremaglio et al. |
| 8,518,024 B2 | 8/2013 | Williams et al. |
| 8,518,052 B2 | 8/2013 | Burgermeister et al. |
| 8,518,062 B2 | 8/2013 | Cole et al. |
| 8,523,939 B1 | 9/2013 | Hausen |
| 8,529,563 B2 | 9/2013 | Long et al. |
| 8,540,744 B2 | 9/2013 | Spivey et al. |
| 8,545,396 B2 | 10/2013 | Cover et al. |
| 8,545,450 B2 | 10/2013 | Voegele et al. |
| 8,551,058 B2 | 10/2013 | Measamer et al. |
| 8,562,513 B2 | 10/2013 | Yamatani |
| 8,562,602 B2 | 10/2013 | Azure |
| 8,568,410 B2 | 10/2013 | Vakharia et al. |
| 8,579,176 B2 | 11/2013 | Smith et al. |
| 8,579,897 B2 | 11/2013 | Vakharia et al. |
| 8,602,970 B2 | 12/2013 | Muyari et al. |
| 8,603,138 B2 | 12/2013 | Faller et al. |
| 8,608,652 B2 | 12/2013 | Voegele et al. |
| 8,617,156 B2 | 12/2013 | Werneth et al. |
| 8,623,011 B2 | 1/2014 | Spivey |
| 8,632,534 B2 | 1/2014 | Pearson et al. |

(56) References Cited

U.S. PATENT DOCUMENTS

| | | |
|---|---|---|
| 8,632,563 B2 | 1/2014 | Nagase et al. |
| 8,636,648 B2 | 1/2014 | Gazdzinski |
| 8,636,650 B2 | 1/2014 | Lee |
| 8,636,730 B2 | 1/2014 | Keppel |
| 8,640,940 B2 | 2/2014 | Ohdaira |
| 8,641,728 B2 | 2/2014 | Stokes et al. |
| 8,652,150 B2 | 2/2014 | Swain et al. |
| 8,657,174 B2 | 2/2014 | Yates et al. |
| 8,663,236 B2 | 3/2014 | Chen et al. |
| 8,668,686 B2 | 3/2014 | Govari et al. |
| 8,679,003 B2 | 3/2014 | Spivey |
| 8,684,967 B2 | 4/2014 | Engel et al. |
| 8,704,923 B2 | 4/2014 | Ogasawara et al. |
| 8,715,281 B2 | 5/2014 | Barlow et al. |
| 8,721,658 B2 | 5/2014 | Kahle et al. |
| 8,723,936 B2 | 5/2014 | Amling et al. |
| 8,727,967 B2 | 5/2014 | Weitzner |
| 8,747,401 B2 | 6/2014 | Gonzalez et al. |
| 8,753,262 B2 | 6/2014 | Sugiyama et al. |
| 8,753,335 B2 | 6/2014 | Moshe et al. |
| 8,764,735 B2 | 7/2014 | Coe et al. |
| 8,771,173 B2 | 7/2014 | Fonger et al. |
| 8,771,260 B2 | 7/2014 | Conlon et al. |
| 8,774,913 B2 | 7/2014 | Demarais et al. |
| 8,784,436 B2 | 7/2014 | Ho et al. |
| 8,795,161 B2 | 8/2014 | Carter |
| 8,821,520 B2 | 9/2014 | Schwemberger et al. |
| 8,821,532 B2 | 9/2014 | Schaeffer |
| 8,828,031 B2 | 9/2014 | Fox et al. |
| 8,834,461 B2 | 9/2014 | Werneth et al. |
| 8,858,590 B2 | 10/2014 | Shelton, IV et al. |
| 8,876,701 B2 | 11/2014 | Surti et al. |
| 8,876,772 B2 | 11/2014 | Weber et al. |
| 8,880,185 B2 | 11/2014 | Hastings et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,920,442 B2 | 12/2014 | Sibbitt, Jr. et al. |
| 8,926,606 B2 | 1/2015 | Davalos et al. |
| 8,932,208 B2 | 1/2015 | Kendale et al. |
| 8,939,897 B2 | 1/2015 | Nobis |
| 8,986,199 B2 | 3/2015 | Weisenburgh, II et al. |
| 8,992,517 B2 | 3/2015 | Davalos et al. |
| 9,005,198 B2 | 4/2015 | Long et al. |
| 9,011,431 B2 | 4/2015 | Long et al. |
| 9,028,483 B2 | 5/2015 | Long et al. |
| 9,049,987 B2 | 6/2015 | Conlon et al. |
| 9,060,782 B2 | 6/2015 | Daniel et al. |
| 9,066,655 B2 | 6/2015 | Stefanchik et al. |
| 9,078,662 B2 | 7/2015 | Bakos et al. |
| 9,084,621 B2 | 7/2015 | Weitzner et al. |
| 9,089,323 B2 | 7/2015 | Bonutti et al. |
| 9,125,557 B2 | 9/2015 | Lien et al. |
| 9,125,631 B2 | 9/2015 | Smith et al. |
| 9,125,639 B2 | 9/2015 | Mathis et al. |
| 9,149,172 B2 | 10/2015 | Iddan et al. |
| 9,155,587 B2 | 10/2015 | Willis et al. |
| 9,186,203 B2 | 11/2015 | Spivey et al. |
| 9,198,733 B2 | 12/2015 | Neal, II et al. |
| 9,220,526 B2 | 12/2015 | Conlon |
| 9,226,772 B2 | 1/2016 | Fox |
| 9,233,241 B2 | 1/2016 | Long |
| 9,248,278 B2 | 2/2016 | Crosby et al. |
| 9,254,169 B2 | 2/2016 | Long et al. |
| 9,265,407 B2 | 2/2016 | Goldfarb et al. |
| 9,271,796 B2 | 3/2016 | Buysse et al. |
| 9,277,957 B2 | 3/2016 | Long et al. |
| 9,295,485 B2 | 3/2016 | Conlon et al. |
| 9,308,049 B2 | 4/2016 | Dejima |
| 9,314,620 B2 | 4/2016 | Long et al. |
| 9,339,328 B2 | 5/2016 | Ortiz et al. |
| 9,345,462 B2 | 5/2016 | Weitzner et al. |
| 9,352,152 B2 | 5/2016 | Lindenthaler et al. |
| 9,370,341 B2 | 6/2016 | Ceniccola et al. |
| 9,375,268 B2 | 6/2016 | Long |
| 9,427,255 B2 | 8/2016 | Griffith et al. |
| 9,486,241 B2 | 11/2016 | Leiner et al. |
| 9,492,148 B2 | 11/2016 | Ginn et al. |
| 9,545,290 B2 | 1/2017 | Tellio et al. |
| 9,549,719 B2 | 1/2017 | Shohat et al. |
| 9,566,126 B2 | 2/2017 | Weitzner et al. |
| 9,572,623 B2 | 2/2017 | Long |
| 9,598,691 B2 | 3/2017 | Davalos |
| 9,627,120 B2 | 4/2017 | Scott et al. |
| 2001/0023333 A1 | 9/2001 | Wise et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0068945 A1 | 6/2002 | Sixto et al. |
| 2002/0082551 A1 | 6/2002 | Yachia et al. |
| 2002/0095164 A1 | 7/2002 | Andreas et al. |
| 2002/0133115 A1 | 9/2002 | Gordon et al. |
| 2002/0138086 A1 | 9/2002 | Sixto et al. |
| 2002/0165592 A1 | 11/2002 | Glukhovsky et al. |
| 2003/0014090 A1 | 1/2003 | Abrahamson |
| 2003/0018373 A1 | 1/2003 | Eckhardt et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0187351 A1 | 10/2003 | Franck et al. |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2004/0002683 A1 | 1/2004 | Nicholson et al. |
| 2004/0024414 A1 | 2/2004 | Downing |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0133089 A1 | 7/2004 | Kilcoyne et al. |
| 2004/0136779 A1 | 7/2004 | Bhaskar |
| 2004/0138529 A1 | 7/2004 | Wiltshire et al. |
| 2004/0138587 A1 | 7/2004 | Lyons |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0225186 A1 | 11/2004 | Horne et al. |
| 2004/0243108 A1 | 12/2004 | Suzuki |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0043690 A1 | 2/2005 | Todd |
| 2005/0059963 A1 | 3/2005 | Phan et al. |
| 2005/0059964 A1 | 3/2005 | Fitz |
| 2005/0065509 A1 | 3/2005 | Coldwell et al. |
| 2005/0070947 A1 | 3/2005 | Franer et al. |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto et al. |
| 2005/0096502 A1 | 5/2005 | Khalili |

(56) References Cited

U.S. PATENT DOCUMENTS

| | | |
|---|---|---|
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131457 A1 | 6/2005 | Douglas et al. |
| 2005/0137454 A1 | 6/2005 | Saadat et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0165272 A1 | 7/2005 | Okada et al. |
| 2005/0165378 A1 | 7/2005 | Heinrich et al. |
| 2005/0165411 A1 | 7/2005 | Orban |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192602 A1 | 9/2005 | Manzo |
| 2005/0209624 A1 | 9/2005 | Vijay |
| 2005/0215858 A1 | 9/2005 | Vail |
| 2005/0216036 A1 | 9/2005 | Nakao |
| 2005/0228224 A1 | 10/2005 | Okada et al. |
| 2005/0228406 A1 | 10/2005 | Bose |
| 2005/0240249 A1 | 10/2005 | Tu et al. |
| 2005/0250987 A1 | 11/2005 | Ewers et al. |
| 2005/0251176 A1 | 11/2005 | Swanstrom et al. |
| 2005/0267492 A1 | 12/2005 | Poncet et al. |
| 2005/0272977 A1 | 12/2005 | Saadat et al. |
| 2005/0274935 A1 | 12/2005 | Nelson |
| 2005/0277956 A1 | 12/2005 | Francese et al. |
| 2005/0288555 A1 | 12/2005 | Binmoeller |
| 2005/0288730 A1* | 12/2005 | Deem ............ A61B 18/1492 607/42 |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0025654 A1 | 2/2006 | Suzuki et al. |
| 2006/0025781 A1 | 2/2006 | Young et al. |
| 2006/0025812 A1 | 2/2006 | Shelton |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0064083 A1 | 3/2006 | Khalaj et al. |
| 2006/0069424 A1 | 3/2006 | Acosta et al. |
| 2006/0069429 A1 | 3/2006 | Spence et al. |
| 2006/0074413 A1 | 4/2006 | Behzadian |
| 2006/0089528 A1 | 4/2006 | Tartaglia et al. |
| 2006/0095031 A1 | 5/2006 | Ormsby |
| 2006/0100687 A1 | 5/2006 | Fahey et al. |
| 2006/0111209 A1 | 5/2006 | Hinman et al. |
| 2006/0111210 A1 | 5/2006 | Hinman |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0161190 A1 | 7/2006 | Gadberry et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0217665 A1 | 9/2006 | Prosek |
| 2006/0217742 A1 | 9/2006 | Messerly et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0253004 A1 | 11/2006 | Frisch et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0287644 A1 | 12/2006 | Inganas et al. |
| 2006/0287666 A1 | 12/2006 | Saadat et al. |
| 2007/0000550 A1 | 1/2007 | Osinski |
| 2007/0005019 A1 | 1/2007 | Okishige |
| 2007/0015965 A1 | 1/2007 | Cox et al. |
| 2007/0032701 A1 | 2/2007 | Fowler et al. |
| 2007/0051375 A1 | 3/2007 | Milliman |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0078439 A1 | 4/2007 | Grandt et al. |
| 2007/0083192 A1 | 4/2007 | Welch et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106317 A1 | 5/2007 | Shelton et al. |
| 2007/0112251 A1 | 5/2007 | Nakhuda |
| 2007/0112342 A1 | 5/2007 | Pearson et al. |
| 2007/0112385 A1 | 5/2007 | Conlon |
| 2007/0112417 A1 | 5/2007 | Shanley et al. |
| 2007/0118115 A1 | 5/2007 | Artale et al. |
| 2007/0123840 A1 | 5/2007 | Cox |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0156028 A1 | 7/2007 | Van Lue et al. |
| 2007/0156116 A1 | 7/2007 | Gonzalez |
| 2007/0161855 A1 | 7/2007 | Mikkaichi et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0191904 A1 | 8/2007 | Libbus et al. |
| 2007/0198057 A1 | 8/2007 | Gelbart et al. |
| 2007/0203398 A1 | 8/2007 | Bonadio et al. |
| 2007/0208336 A1 | 9/2007 | Kim et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0233040 A1 | 10/2007 | Macnamara et al. |
| 2007/0244356 A1 | 10/2007 | Carrillo et al. |
| 2007/0244358 A1 | 10/2007 | Lee |
| 2007/0255303 A1 | 11/2007 | Bakos et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270907 A1 | 11/2007 | Stokes et al. |
| 2007/0282165 A1 | 12/2007 | Hopkins et al. |
| 2008/0004650 A1 | 1/2008 | George |
| 2008/0015413 A1 | 1/2008 | Barlow et al. |
| 2008/0021416 A1 | 1/2008 | Arai et al. |
| 2008/0022927 A1 | 1/2008 | Zhang et al. |
| 2008/0027387 A1 | 1/2008 | Grabinsky |

(56) References Cited

U.S. PATENT DOCUMENTS

| | | |
|---|---|---|
| 2008/0033244 A1 | 2/2008 | Matsui et al. |
| 2008/0058586 A1 | 3/2008 | Karpiel |
| 2008/0065169 A1 | 3/2008 | Colliou et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0103527 A1 | 5/2008 | Martin et al. |
| 2008/0114384 A1 | 5/2008 | Chang et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0140069 A1 | 6/2008 | Filloux et al. |
| 2008/0140071 A1 | 6/2008 | Vegesna |
| 2008/0147056 A1 | 6/2008 | van der Weide et al. |
| 2008/0150754 A1 | 6/2008 | Quendt |
| 2008/0171907 A1 | 7/2008 | Long et al. |
| 2008/0188710 A1 | 8/2008 | Segawa et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0214890 A1 | 9/2008 | Motai et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0243148 A1 | 10/2008 | Mikkaichi et al. |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0287801 A1 | 11/2008 | Magnin et al. |
| 2008/0300461 A1 | 12/2008 | Shaw et al. |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0078736 A1 | 3/2009 | Van Lue |
| 2009/0082627 A1 | 3/2009 | Karasawa et al. |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0163770 A1 | 6/2009 | Torrie et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0210000 A1 | 8/2009 | Sullivan et al. |
| 2009/0221873 A1 | 9/2009 | McGrath |
| 2009/0228001 A1 | 9/2009 | Pacey |
| 2009/0259105 A1 | 10/2009 | Miyano et al. |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0036198 A1 | 2/2010 | Tacchino et al. |
| 2010/0048990 A1 | 2/2010 | Bakos |
| 2010/0049223 A1 | 2/2010 | Granja Filho |
| 2010/0056862 A1 | 3/2010 | Bakos |
| 2010/0076451 A1 | 3/2010 | Zwolinski et al. |
| 2010/0081875 A1 | 4/2010 | Fowler et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0191050 A1 | 7/2010 | Zwolinski |
| 2010/0191267 A1 | 7/2010 | Fox |
| 2010/0198248 A1 | 8/2010 | Vakharia |
| 2010/0210906 A1 | 8/2010 | Wendlandt |
| 2010/0217367 A1 | 8/2010 | Belson |
| 2010/0249700 A1 | 9/2010 | Spivey |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2011/0077476 A1 | 3/2011 | Rofougaran et al. |
| 2011/0087224 A1 | 4/2011 | Cadeddu et al. |
| 2011/0093009 A1 | 4/2011 | Fox |
| 2011/0098694 A1 | 4/2011 | Long |
| 2011/0098704 A1 | 4/2011 | Long et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0152610 A1 | 6/2011 | Trusty et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0245619 A1 | 10/2011 | Holcomb |
| 2011/0282149 A1 | 11/2011 | Vargas et al. |
| 2011/0284014 A1 | 11/2011 | Cadeddu et al. |
| 2012/0029335 A1 | 2/2012 | Sudam et al. |
| 2012/0078266 A1 | 3/2012 | Tyson, Jr. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0109122 A1 | 5/2012 | Arena et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0191075 A1 | 7/2012 | Trusty |
| 2012/0191076 A1 | 7/2012 | Voegele et al. |
| 2012/0289857 A1 | 11/2012 | Toth et al. |
| 2013/0030430 A1 | 1/2013 | Stewart et al. |
| 2013/0090666 A1 | 4/2013 | Hess et al. |
| 2013/0158348 A1 | 6/2013 | Nobis et al. |
| 2013/0245356 A1 | 9/2013 | Fernandez et al. |
| 2013/0331646 A1 | 12/2013 | Pell et al. |
| 2013/0331649 A1 | 12/2013 | Khait et al. |
| 2014/0039491 A1 | 2/2014 | Bakos et al. |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2015/0032132 A1 | 1/2015 | Harris et al. |
| 2015/0230858 A1 | 8/2015 | Long et al. |
| 2015/0265335 A1 | 9/2015 | Bakos et al. |
| 2015/0374444 A1 | 12/2015 | Conlon et al. |
| 2016/0074056 A1 | 3/2016 | Conlon |
| 2016/0100879 A1 | 4/2016 | Long |
| 2016/0128759 A1 | 5/2016 | Long et al. |
| 2016/0166311 A1 | 6/2016 | Long et al. |
| 2016/0296280 A1 | 10/2016 | Long |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |

(56) References Cited

FOREIGN PATENT DOCUMENTS

| | | |
|---|---|---|
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1477104 B1 | 1/2009 |
| EP | 0723462 B1 | 3/2009 |
| EP | 1769749 B1 | 11/2009 |
| EP | 2135545 A2 | 12/2009 |
| EP | 1769766 B1 | 2/2010 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | S63309252 A | 12/1988 |
| JP | H0438960 A | 2/1992 |
| JP | H06269460 A | 9/1994 |
| JP | H0829699 A | 2/1996 |
| JP | H0975365 A | 3/1997 |
| JP | H1024049 A | 1/1998 |
| JP | 3007713 B2 | 2/2000 |
| JP | 2000107197 A | 4/2000 |
| JP | 2000245683 A | 9/2000 |
| JP | 2001526072 A | 12/2001 |
| JP | 2002369791 A | 12/2002 |
| JP | 2003088494 A | 3/2003 |
| JP | 2003235852 A | 8/2003 |
| JP | 2004033525 A | 2/2004 |
| JP | 2004065745 A | 3/2004 |
| JP | 2005121947 A | 5/2005 |
| JP | 2005261514 A | 9/2005 |
| JP | 2005296063 A | 10/2005 |
| JP | 2006297005 A | 11/2006 |
| JP | 2006343510 A | 12/2006 |
| JP | 2007020806 A | 2/2007 |
| JP | 2007125264 A | 5/2007 |
| JP | 2007516792 A | 6/2007 |
| JP | 2010503496 A | 2/2010 |
| JP | 5646674 B2 | 12/2014 |
| NL | 1021295 C2 | 2/2004 |
| SU | 194230 | 5/1967 |
| SU | 980703 A1 | 12/1982 |
| WO | 8401707 A1 | 5/1984 |
| WO | 8607543 A1 | 12/1986 |
| WO | 9213494 A1 | 8/1992 |
| WO | 9310850 A1 | 6/1993 |
| WO | 9320760 A1 | 10/1993 |
| WO | 9320765 A1 | 10/1993 |
| WO | 9422383 A1 | 10/1994 |
| WO | 9509666 A1 | 4/1995 |
| WO | 9622056 A1 | 7/1996 |
| WO | 9627331 A1 | 9/1996 |
| WO | 9639946 A1 | 12/1996 |
| WO | 9712557 A1 | 4/1997 |
| WO | 9801080 A1 | 1/1998 |
| WO | 9900060 A1 | 1/1999 |
| WO | 9909919 A1 | 3/1999 |
| WO | 9917661 A1 | 4/1999 |
| WO | 9930622 A2 | 6/1999 |
| WO | 0022996 A1 | 4/2000 |
| WO | 0035358 A1 | 6/2000 |
| WO | 0068665 A1 | 11/2000 |
| WO | 0110319 A1 | 2/2001 |
| WO | 0126708 A1 | 4/2001 |
| WO | 0141627 A2 | 6/2001 |
| WO | 0158360 A2 | 8/2001 |
| WO | 0211621 A2 | 2/2002 |
| WO | 0234122 A2 | 5/2002 |
| WO | 02094082 A2 | 11/2002 |
| WO | 03045260 A1 | 6/2003 |
| WO | 03047684 A2 | 6/2003 |
| WO | 03059412 A2 | 7/2003 |
| WO | 03078721 A2 | 9/2003 |
| WO | 03081761 A2 | 10/2003 |
| WO | 03082129 A2 | 10/2003 |
| WO | 2004006789 A1 | 1/2004 |
| WO | 2004028613 A2 | 4/2004 |
| WO | 2004037123 A1 | 5/2004 |
| WO | 2004037149 A1 | 5/2004 |
| WO | 2004052221 A1 | 6/2004 |
| WO | 2004086984 A1 | 10/2004 |
| WO | 2005009211 A2 | 2/2005 |
| WO | 2005018467 A2 | 3/2005 |
| WO | 2005037088 A2 | 4/2005 |
| WO | 2005048827 A1 | 6/2005 |
| WO | 2005065284 A2 | 7/2005 |
| WO | 2005097019 A2 | 10/2005 |
| WO | 2005097234 A2 | 10/2005 |
| WO | 2005112810 A2 | 12/2005 |
| WO | 2005120363 A1 | 12/2005 |
| WO | 2005122866 A1 | 12/2005 |
| WO | 2006007399 A1 | 1/2006 |
| WO | 2006012630 A2 | 2/2006 |
| WO | 2006040109 A1 | 4/2006 |
| WO | 2006041881 A2 | 4/2006 |
| WO | 2006060405 A2 | 6/2006 |
| WO | 2006110733 A2 | 10/2006 |
| WO | 2006113216 A2 | 10/2006 |
| WO | 2007013059 A2 | 2/2007 |
| WO | 2007014063 A2 | 2/2007 |
| WO | 2007035537 A2 | 3/2007 |
| WO | 2007048085 A2 | 4/2007 |
| WO | 2007063550 A2 | 6/2007 |
| WO | 2007100067 A1 | 9/2007 |
| WO | 2007109171 A2 | 9/2007 |
| WO | 2007135577 A2 | 11/2007 |
| WO | 2007143200 A2 | 12/2007 |
| WO | 2007144004 A1 | 12/2007 |
| WO | 2008005433 A1 | 1/2008 |
| WO | 2008033356 A2 | 3/2008 |
| WO | 2008034103 A2 | 3/2008 |
| WO | 2008041225 A2 | 4/2008 |
| WO | 2008076337 A1 | 6/2008 |

(56) References Cited

FOREIGN PATENT DOCUMENTS

| WO | 2008076800 A2 | 6/2008 |
|---|---|---|
| WO | 2008079440 A2 | 7/2008 |
| WO | 2008080062 A2 | 7/2008 |
| WO | 2008101075 A2 | 8/2008 |
| WO | 2008101086 A2 | 8/2008 |
| WO | 2008102154 A2 | 8/2008 |
| WO | 2008108863 A2 | 9/2008 |
| WO | 2008151237 A1 | 12/2008 |
| WO | 2009021030 A1 | 2/2009 |
| WO | 2009027065 A1 | 3/2009 |
| WO | 2009029065 A1 | 3/2009 |
| WO | 2009032623 A2 | 3/2009 |
| WO | 2009036457 A1 | 3/2009 |
| WO | 2009121017 A1 | 10/2009 |
| WO | 2009132190 A2 | 10/2009 |
| WO | 2010027688 A1 | 3/2010 |
| WO | 2010056716 A2 | 5/2010 |
| WO | 2010080974 A1 | 7/2010 |
| WO | 2010088481 A1 | 8/2010 |
| WO | 2012031204 A2 | 3/2012 |
| WO | 2012071526 A2 | 5/2012 |
| WO | 2013044378 A1 | 4/2013 |

OTHER PUBLICATIONS

"Ethicon Endo-Surgery Studies Presented At DDW Demonstrate Potential Of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at Sages Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular laparo . . . ; accessed Jan. 5, 2010 (4 pages).
Hakko Retractors, obtained Aug. 25, 2009 (5 pages).
Zadno et al., "Linear Superelasticity in Cold-Worked Ni—Ti," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.
Widera et al., "Increased DNA Vaccine Delivery and Immunogenicity by Electroporation In Vivo," The Journal of Immunology, 164, pp. 4635-4640 (2000).
Davalos, et al., "Tissue Ablation with Irreversible Electroporation," Annals of Biomedical Engineering, 33.2 (2005): 223-231.

Maxim Integrated Application Note 3977: Class D Amplifiers: Fundamentals of Operation and Recent Developments, Jan. 31, 2007.
International Search Report for PCT/US2010/020465, dated Jun. 30, 2010 (6 pages).
Written Opinion for PCT/US2010/020465, dated Jun. 30, 2010 (9 pages).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 376-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radio!, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastomosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastomotic Device for Flexible Endoscopy," Gastrointestinal Endosc, (2003), vol. 58(4), pp. 585-591.

(56) References Cited

OTHER PUBLICATIONS

G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 533-840.
CRE™ A Pulmonary Balloon Dilator; [online] URL: http://www.bostonscientific.com/Device.bsci?page=HCP_Overview &navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklav?i? et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).

* cited by examiner

ELECTRICAL ABLATION DEVICES

CROSS REFERENCE TO RELATED APPLICATIONS

This non-provisional patent application is a continuation patent application claiming priority under 35 U.S.C. § 120 of U.S. patent application Ser. No. 13/602,742, filed Sep. 4, 2012, entitled ELECTRICAL ABLATION DEVICES, now U.S. Patent Application Publication No. 2012/0330306, which is a divisional patent application claiming priority under 35 U.S.C. § 121 of U.S. patent application Ser. No. 12/352,375, filed Jan. 12, 2009, entitled ELECTRICAL ABLATION DEVICES, now U.S. Pat. No. 8,361,066, the entire disclosures of which are hereby incorporated by reference herein.

BACKGROUND

Electrical ablation therapy has been employed in medicine for the treatment of undesirable tissue such as diseased tissue, cancer, malignant and benign tumors, masses, lesions, and other abnormal tissue growths. While conventional apparatuses, systems, and methods for the electrical ablation of undesirable tissue are effective, one drawback with conventional electrical ablation treatment is the resulting permanent damage that may occur to the healthy tissue surrounding the abnormal tissue due primarily to the detrimental thermal effects resulting from exposing the tissue to thermal energy generated by the electrical ablation device. This may be particularly true when exposing the tissue to electric potentials sufficient to cause cell necrosis using high temperature thermal therapies including focused ultrasound ablation, radiofrequency (RF) ablation, or interstitial laser coagulation. Other techniques for tissue ablation include chemical ablation, in which chemical agents are injected into the undesirable tissue to cause ablation as well as surgical excision, cryotherapy, radiation, photodynamic therapy, Moh's micrographic surgery, topical treatments with 5-fluorouracil, laser ablation. Other drawbacks of conventional thermal, chemical, and other ablation therapy are cost, length of recovery, and the extraordinary pain inflicted on the patient.

Conventional thermal, chemical, and other ablation techniques have been employed for the treatment of a variety of undesirable tissue. Thermal and chemical ablation techniques have been used for the treatment of varicose veins resulting from reflux disease of the greater saphenous vein (GSV), in which the varicose vein is stripped and then is exposed to either chemical or thermal ablation. Other techniques for the treatment of undesirable tissue are more radical. Prostate cancer, for example, may be removed using a prostatectomy, in which the entire or part of prostate gland and surrounding lymph nodes are surgically removed. Like most other forms of cancer, radiation therapy may be used in conjunction with or as an alternate method for the treatment of prostate cancer. Another thermal ablation technique for the treatment of prostate cancer is RF interstitial tumor ablation (RITA) via trans-rectal ultrasound guidance. While these conventional methods for the treatment of prostate cancer are effective, they are not preferred by many surgeons and may result in detrimental thermal effects to healthy tissue surrounding the prostate. Similar thermal ablation techniques may be used for the treatment of basal cell carcinoma (BCC) tissue, a slowly growing cutaneous malignancy derived from the rapidly proliferating basal layer of the epidermis. BCC tissue in tumors ranging in size from about 5 mm to about 40 mm may be thermally ablated with a pulsed carbon dioxide laser. Nevertheless, carbon dioxide laser ablation is a thermal treatment method and may cause permanent damage to healthy tissue surrounding the BCC tissue. Furthermore, this technique requires costly capital investment in carbon dioxide laser equipment. Undesirable tissue growing inside a body lumen such as the esophagus, large bowel, or in cavities formed in solid tissue such as the breast, for example, can be difficult to destroy using conventional ablation techniques. Surgical removal of undesirable tissue, such as a malignant or benign tumor, from the breast is likely to leave a cavity. Surgical resection of residual intralumenal tissue may remove only a portion of the undesirable tissue cells within a certain margin of healthy tissue. Accordingly, some undesirable tissue is likely to remain within the wall of the cavity due to the limitation of conventional ablation instrument configurations, which may be effective for treating line-of-sight regions of tissue, but may be less effective for treating the residual undesirable tissue.

Accordingly, there remains a need for improved electrical ablation apparatuses, systems, and methods for the treatment of undesirable tissue found in diseased tissue, cancer, malignant and benign tumors, masses, lesions, and other abnormal tissue growths. There remains a need for minimally invasive treatment of undesirable tissue through the use of irreversible electroporation (IRE) ablation techniques without causing the detrimental thermal effects of conventional thermal ablation techniques.

FIGURES

The novel features of the various described embodiments are set forth with particularity in the appended claims. The various embodiments, however, both as to organization and methods of operation, together with advantages thereof, may be understood in accordance with the following description taken in conjunction with the accompanying drawings as follows.

FIG. 1 illustrates one embodiment of an electrical ablation system.

FIGS. 2A-D illustrate one embodiment of the electrical ablation device in various phases of deployment.

Figures 6, 7:
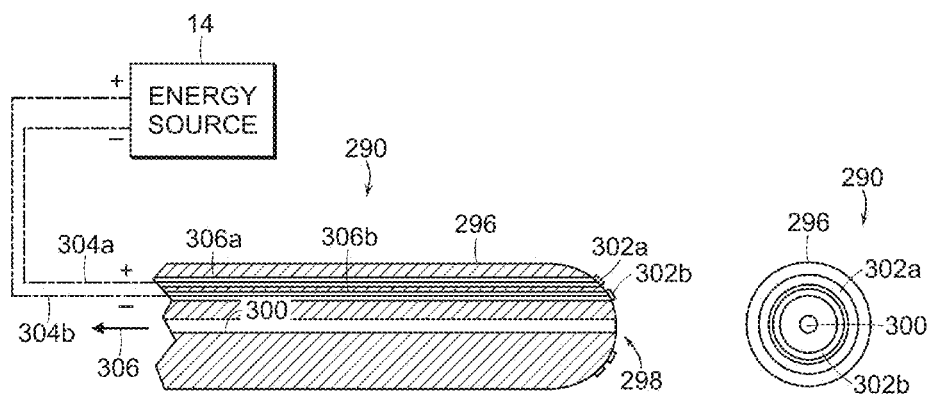
Figure 8:
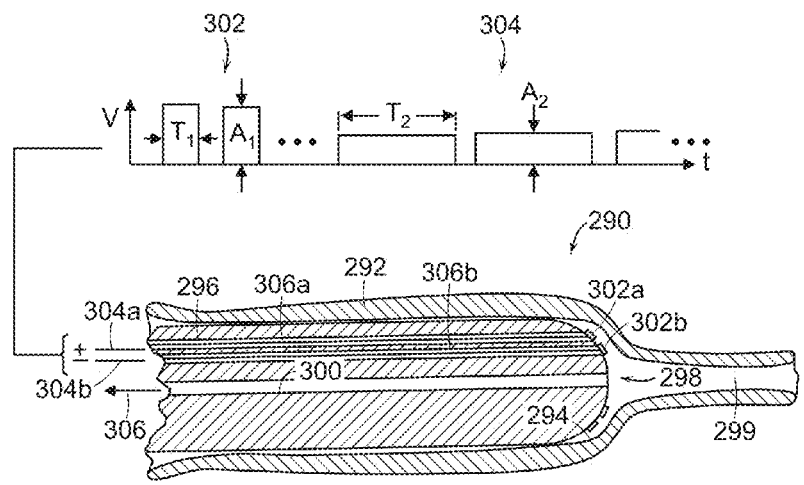

FIGS. 6, 7, and 8 illustrate one embodiment of an electrical ablation device to treat undesirable tissue within body lumen using electrical energy, where FIG. 6 illustrates a sectioned view of one embodiment of an electrical ablation device, FIG. 7 illustrates an end view of one embodiment of the electrical ablation device shown in FIG. 6, and FIG. 8 illustrates a cross-sectional view of one embodiment of the electrical ablation device shown in FIG. 6.

Figure 9:
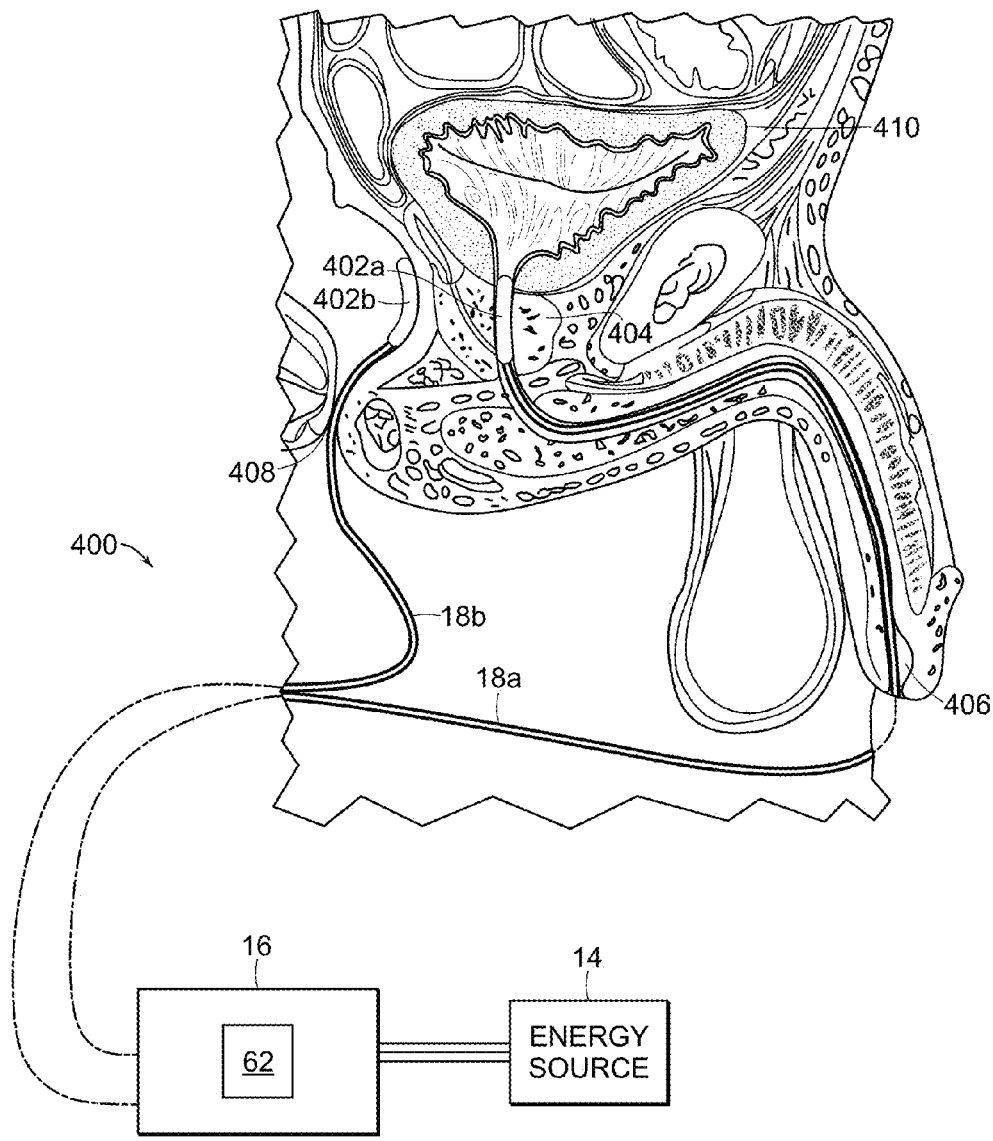

FIG. 9 illustrates one embodiment of an electrical ablation system in use to treat non-metastatic prostate cancer in a patient.

Figure 10:
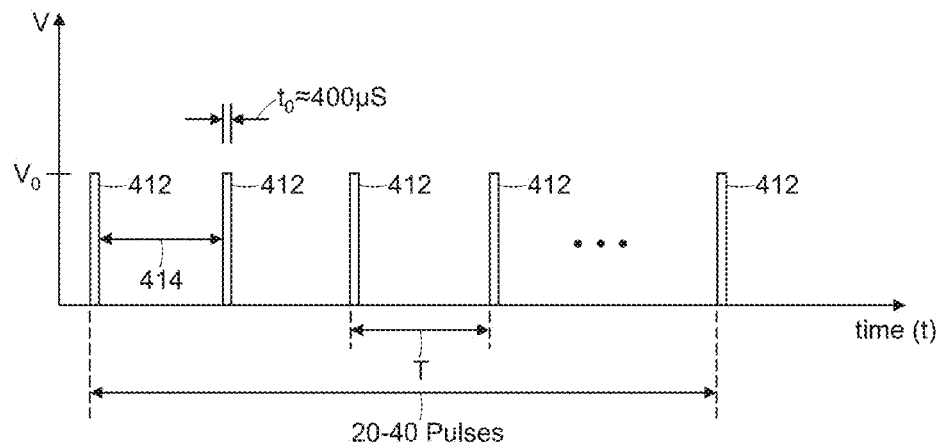

FIG. 10 is a graphical representation of a series of electrical pulses that may be applied to undesirable tissue to induce irreversible electroporation suitable to ablate non-metastatic cancer of the prostrate as described in FIG. 9.

Figure 1:
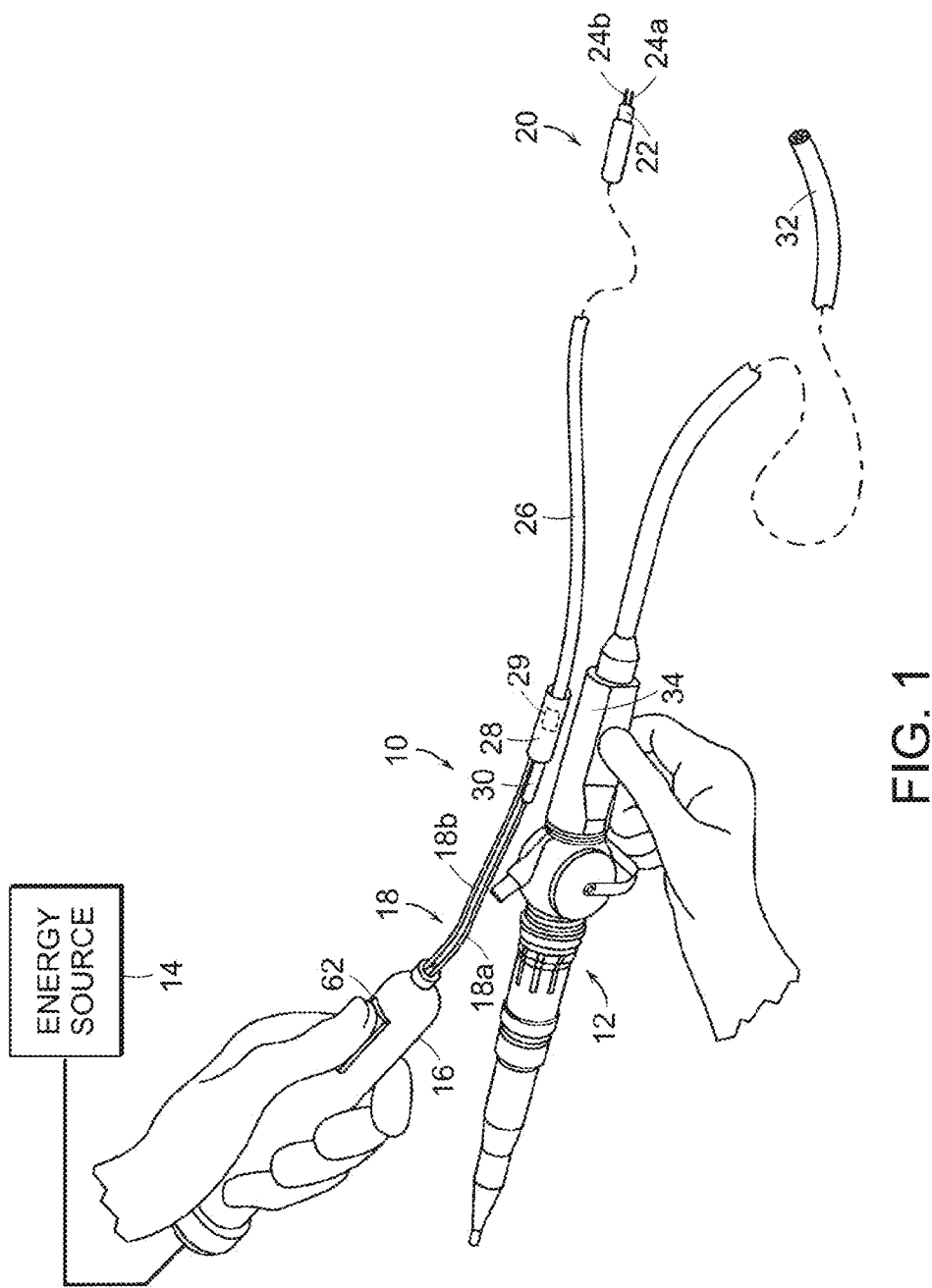
Figure 11:
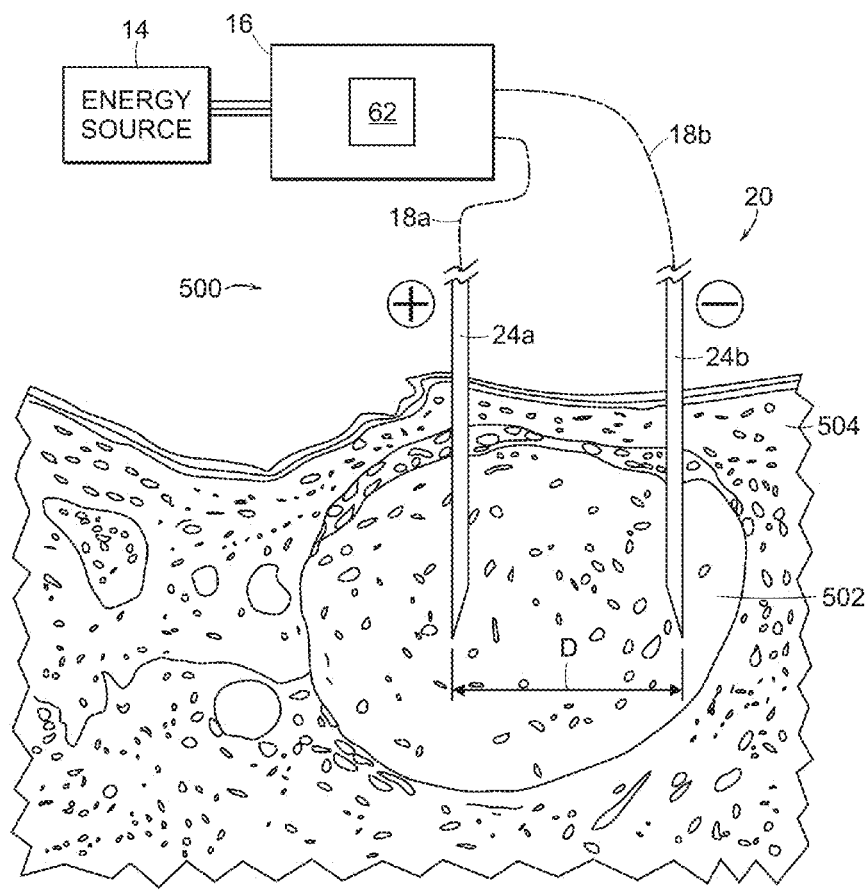

FIG. 11 illustrates one embodiment of the electrical ablation system described FIG. 1 in use to treat basal cell carcinoma (BCC) tissue.

Figure 12:
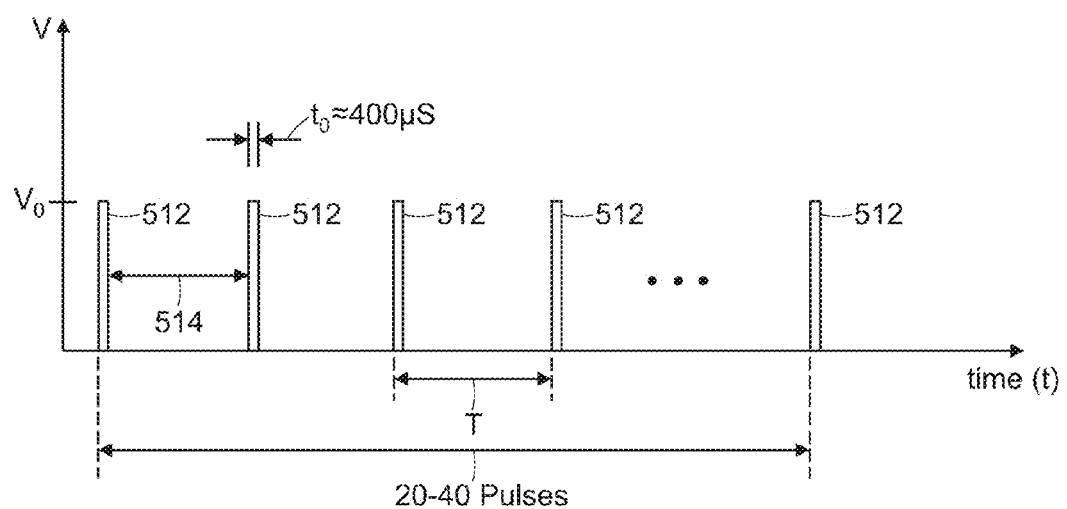

FIG. 12 is a graphical representation of a series of electrical pulses for treating basal cell carcinoma (BCC) tissue as shown in FIG. 11 with irreversible electroporation energy.

Figure 13A:
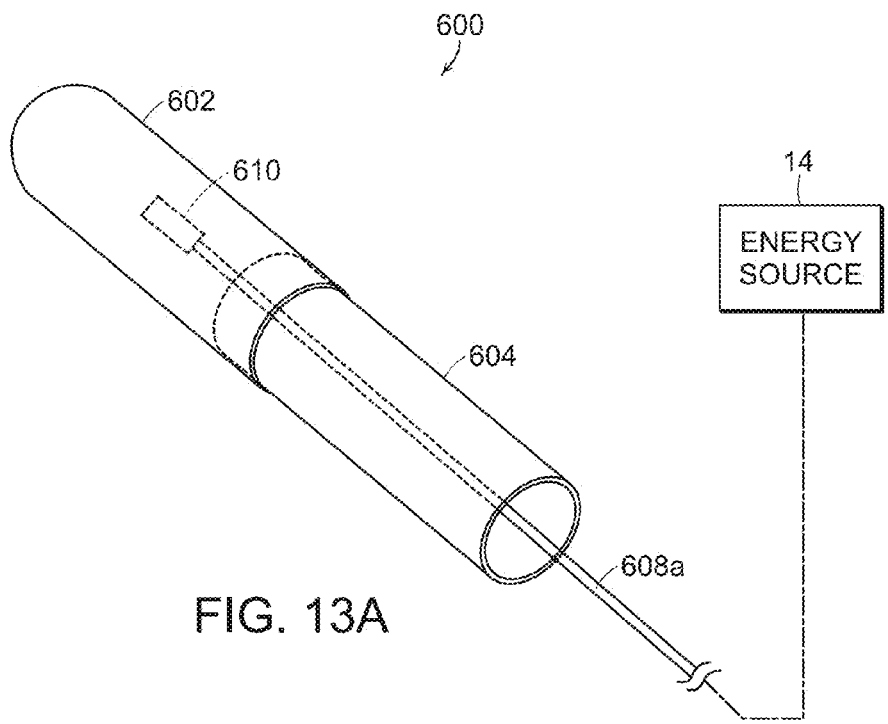

FIG. 13A illustrates one embodiment of an electrical ablation device, in a collapsed state, the device having a configuration suitable for the treatment of abnormal tissue located in a lumen, abscess, void, or cavity.

Figure 13B:
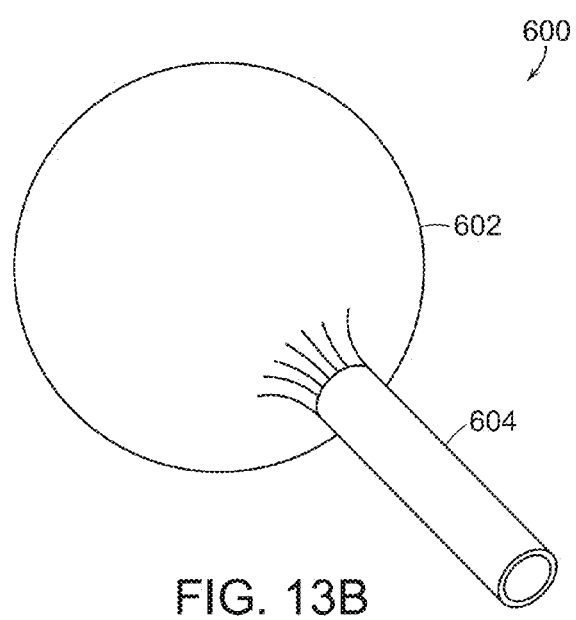

FIG. 13B illustrates one embodiment of the electrical ablation device shown in FIG. 13A, in an inflated state, the device having a configuration suitable for the treatment of abnormal tissue located in a lumen, abscess, void, or cavity.

Figure 14:
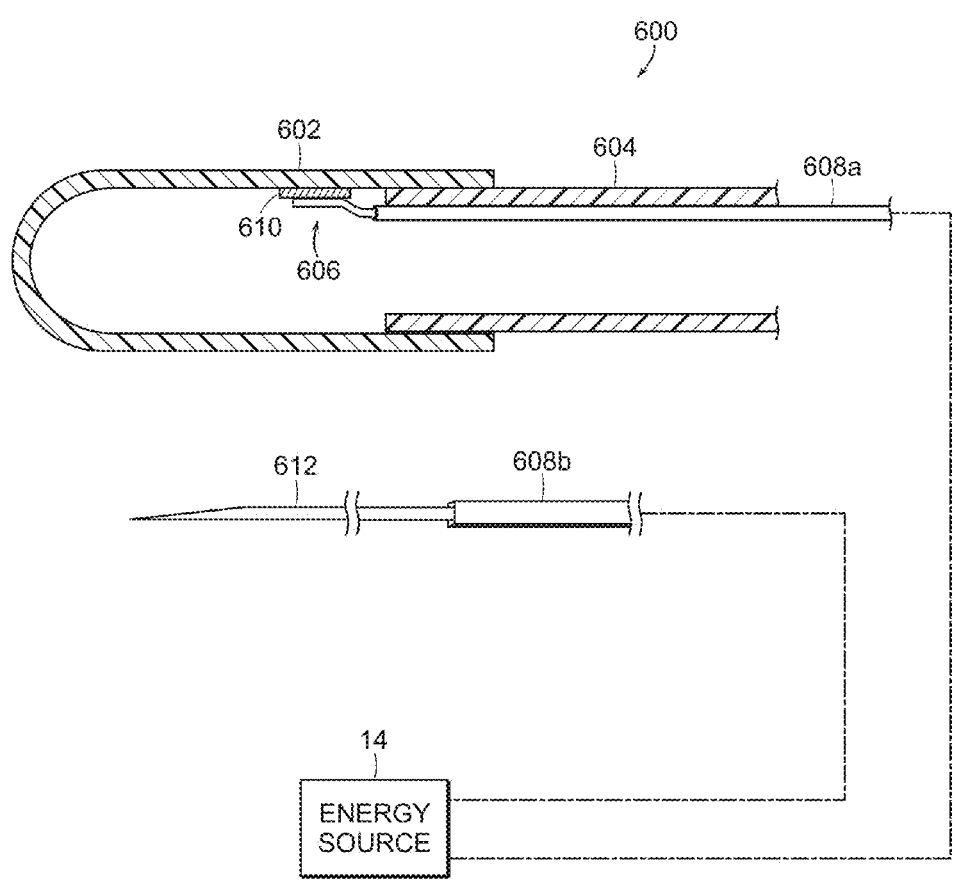

FIG. 14 is a cross-sectional view of the electrical ablation device showing a cross-sectional view of the conductive elastomer electrode and the non-conductive catheter shown in FIGS. 13A and 13B.

Figure 15:
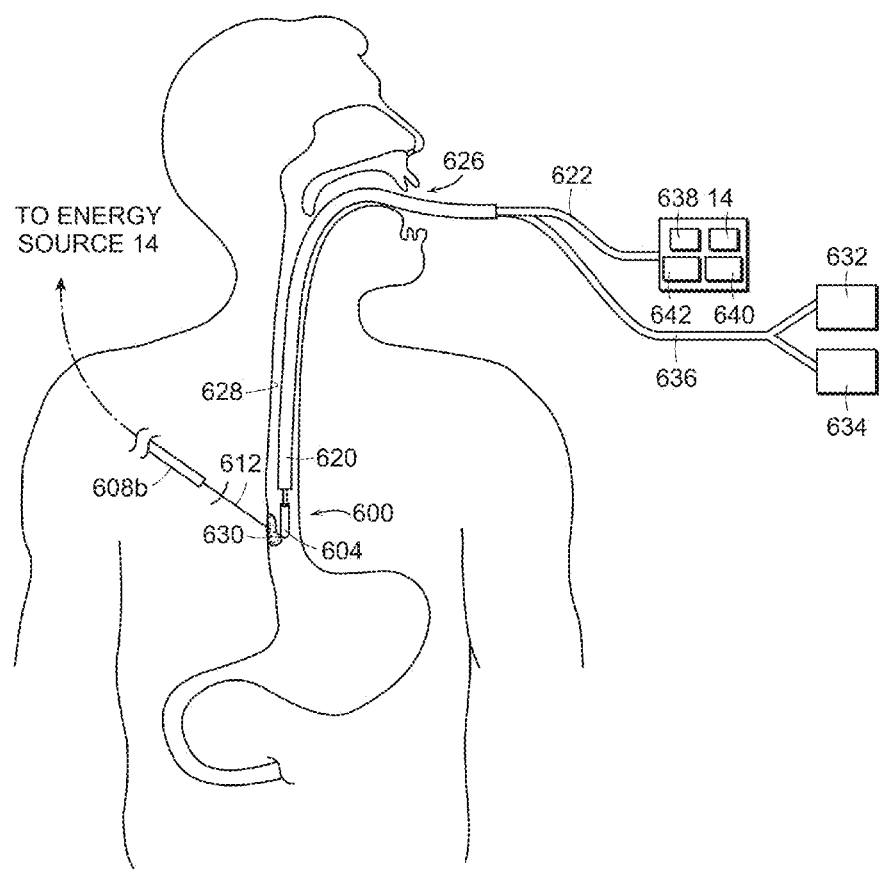

FIG. 15 illustrates one embodiment of the electrical ablation device shown in FIG. 13A inserted through the mouth and esophagus to ablate cancerous tissue in the esophagus using electrical pulses.

Figure 16:
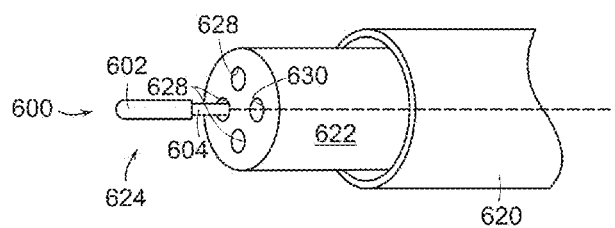

FIG. 16 illustrates a distal portion of an endoscope used in conjunction with the electrical ablation device shown in FIG. 13A.

Figure 17:
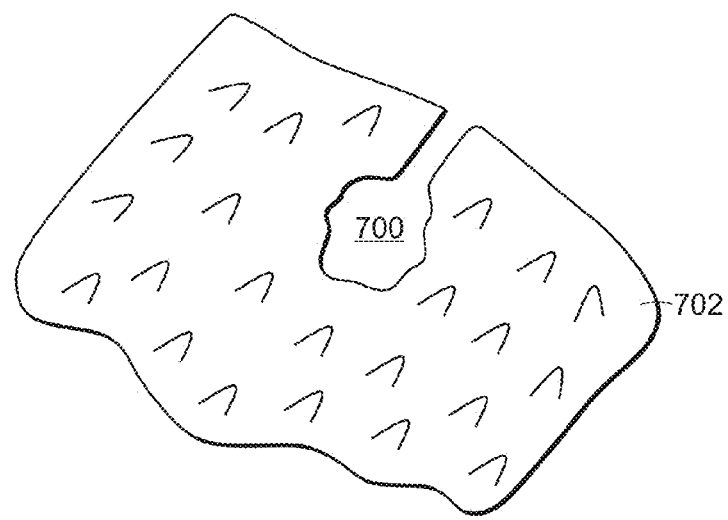

FIG. 17 illustrates a cross-sectional view of a breast showing a cavity that may be left after a lumpectomy to remove a tumor from the breast.

Figure 18:
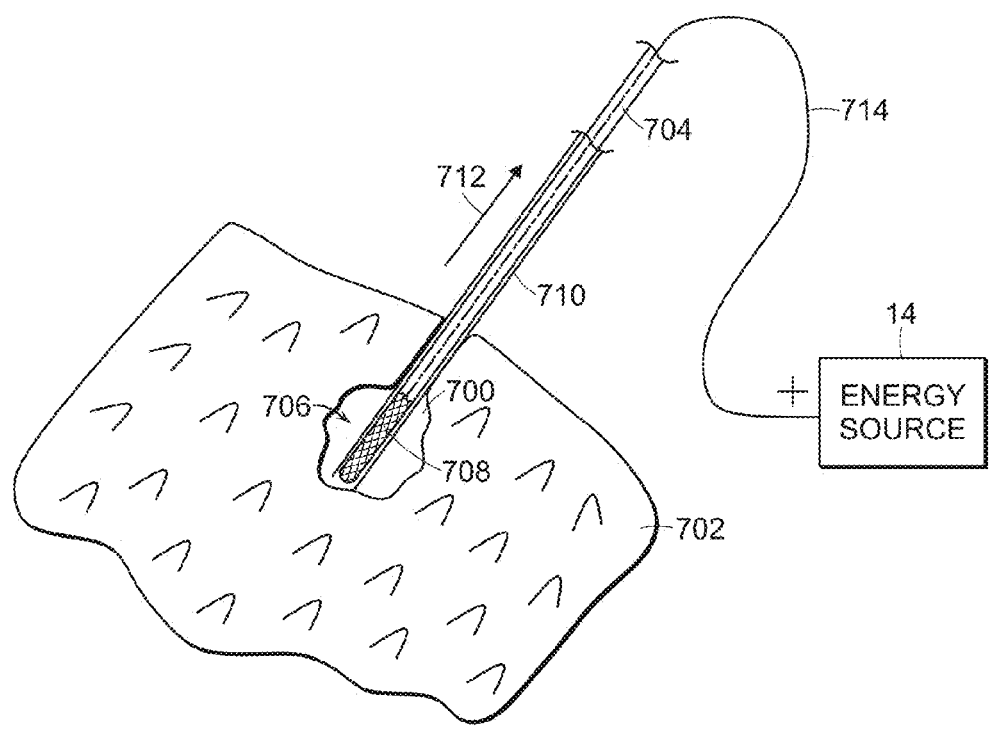

FIG. 18 illustrates one embodiment of a catheter inserted into the cavity left in the breast following a lumpectomy procedure as shown in FIG. 17.

Figure 19:
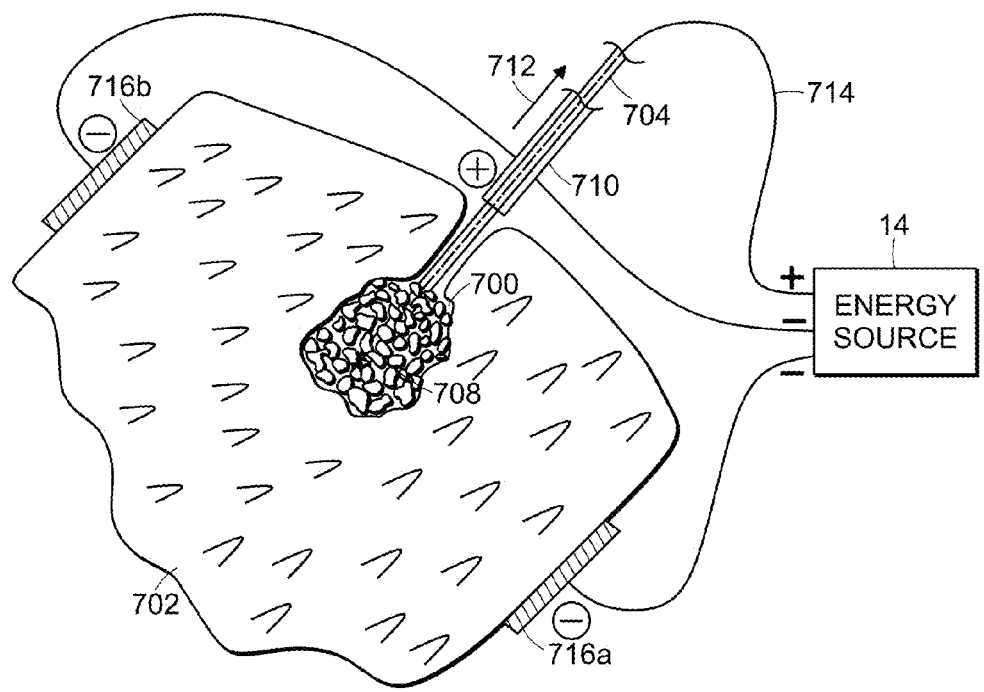

FIG. 19 illustrates an expanded sponge filling the cavity left in the breast following a lumpectomy as shown in FIG. 17.

Figure 20:
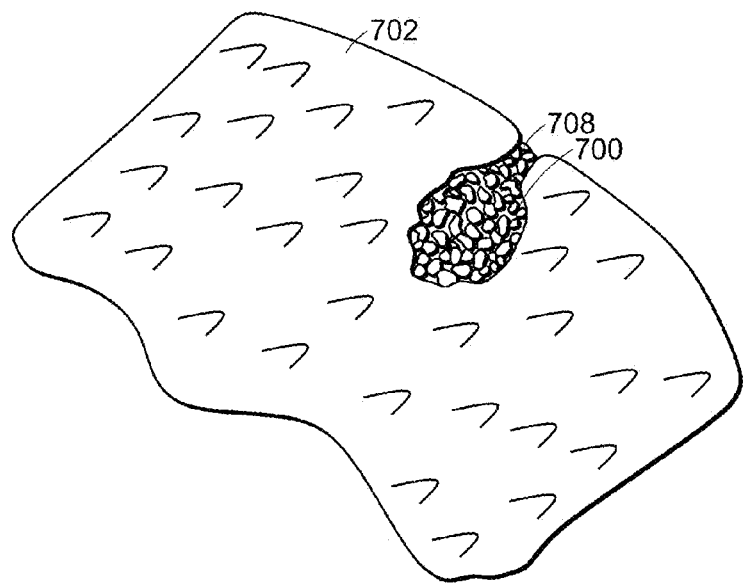

FIG. 20 illustrates the expanded sponge intact to fill the cavity left in the breast as shown in FIG. 17 following irreversible electroporation ablation therapy.

Figure 21:
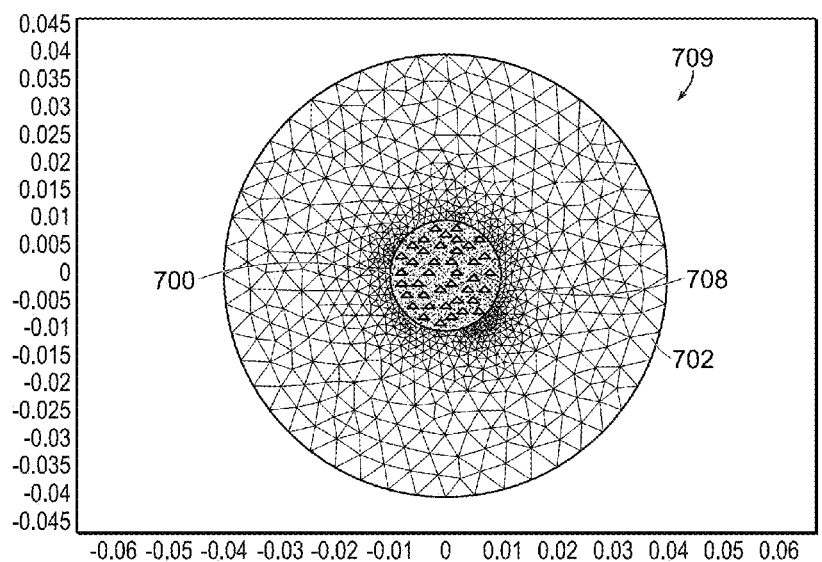

FIG. 21 illustrates a mesh of a finite element model of a sponge inserted in the cavity left in the breast as shown in FIG. 17.

Figure 22:
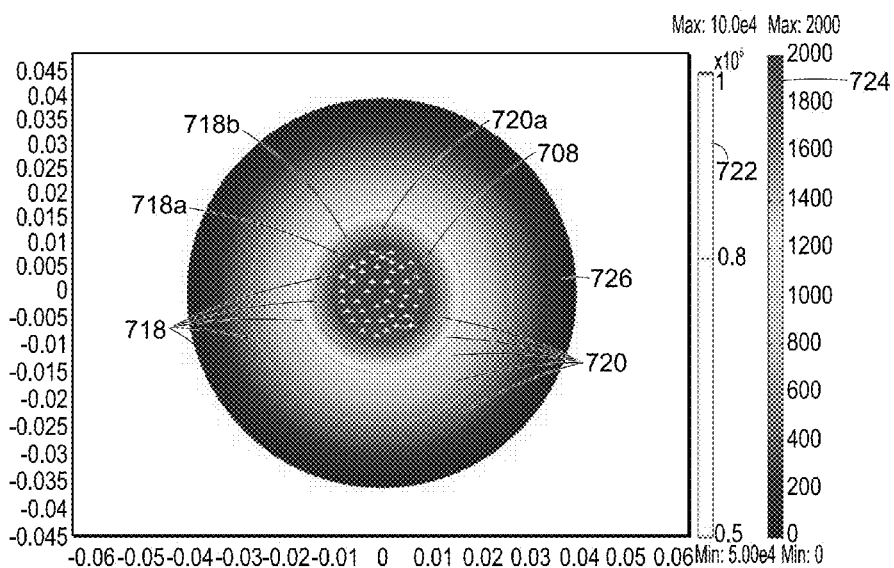

FIG. 22 is a graphical representation of electric potential and electrical field strength sufficient to induce irreversible electroporation when applied to the sponge located within the breast cavity as shown in FIG. 17.

Figure 23:
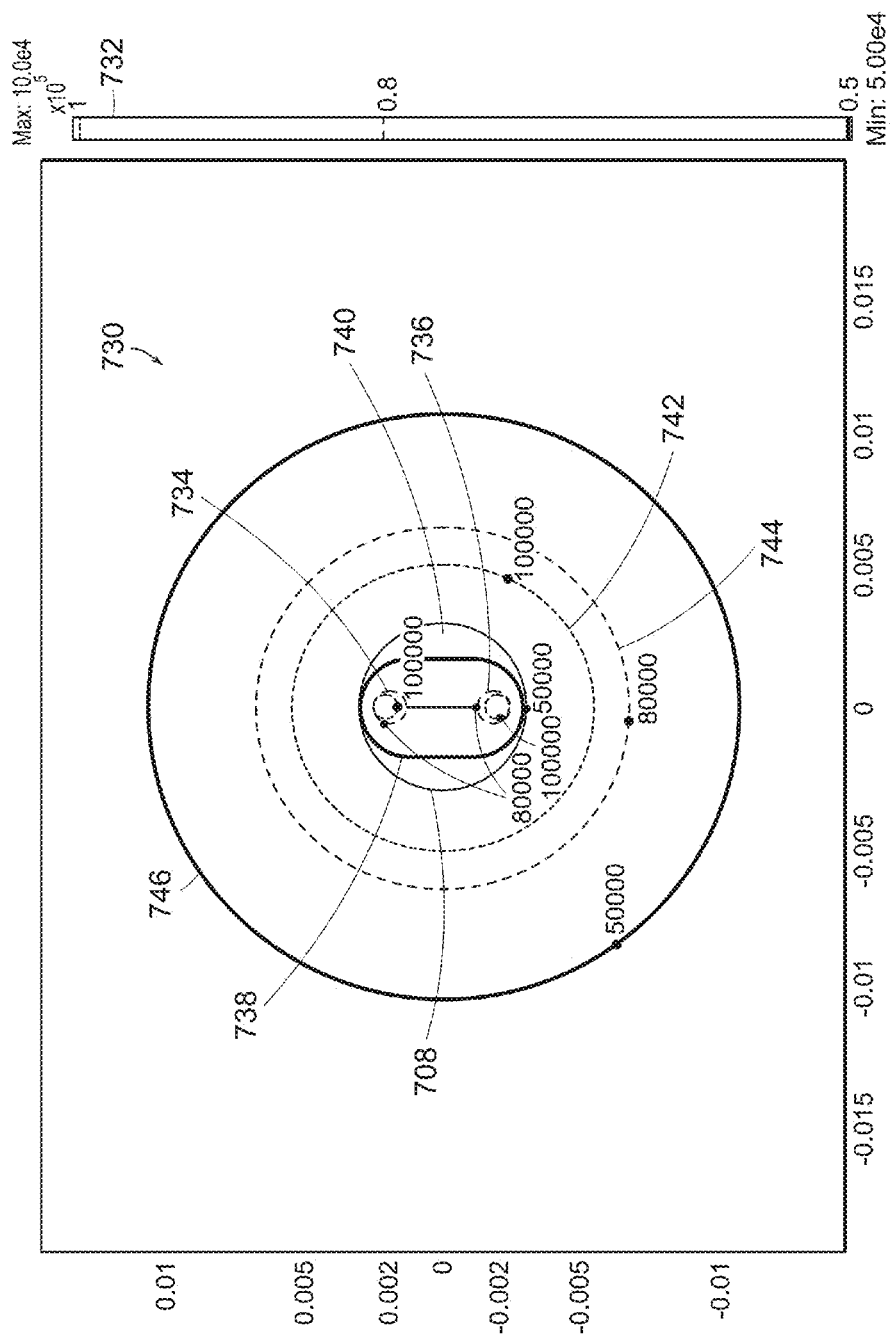

FIG. 23 is a graphical representation of electric field strength contours in volts per meter (V/m) developed when electrodes are energized by an energy source.

DESCRIPTION

Various embodiments are directed to apparatuses, systems, and methods for the electrical ablation treatment of undesirable tissue such as diseased tissue, cancer, malignant and benign tumors, masses, lesions, and other abnormal tissue growths without causing any detrimental thermal effects to surrounding healthy tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without the specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments of apparatuses, systems, and methods for the electrical ablation treatment of undesirable tissue such as diseased tissue, cancer, malignant and benign tumors, masses, lesions, and other abnormal tissue growths, are described throughout the specification and illustrated in the accompanying drawings. The electrical ablation devices in accordance with the described embodiments may comprise one or more electrodes configured to be positioned into or proximal to undesirable tissue in a tissue treatment region (e.g., target site, worksite) where there is evidence of abnormal tissue growth, for example. In general, the electrodes comprise an electrically conductive portion (e.g., medical grade stainless steel) and are configured to electrically couple to an energy source. Once the electrodes are positioned into or proximal to the undesirable tissue, an energizing potential is applied to the electrodes to create an electric field to which the undesirable tissue is exposed. The energizing potential (and the resulting electric field) may be characterized by multiple parameters such as frequency, amplitude, pulse width (duration of a pulse or pulse length), and/or polarity. Depending on the diagnostic or therapeutic treatment to be rendered, a particular electrode may be configured either as an anode (+) or a cathode (−) or may comprise a plurality of electrodes with at least one configured as an anode and at least one other configured as a cathode. Regardless of the initial polar configuration, the polarity of the electrodes may be reversed by reversing the polarity of the output of the energy source.

In various embodiments, a suitable energy source may comprise an electrical waveform generator, which may be configured to create an electric field that is suitable to create irreversible electroporation in undesirable tissue at various electric filed amplitudes and durations. The energy source may be configured to deliver irreversible electroporation pulses in the form of direct-current (DC) and/or alternating-current (AC) voltage potentials (e.g., time-varying voltage potentials) to the electrodes. The irreversible electroporation pulses may be characterized by various parameters such as frequency, amplitude, pulse length, and/or polarity. The undesirable tissue may be ablated by exposure to the electric potential difference across the electrodes.

In one embodiment, the energy source may comprise a wireless transmitter to deliver energy to the electrodes using wireless energy transfer techniques via one or more remotely positioned antennas. Those skilled in the art will appreciate that wireless energy transfer or wireless power transmission is the process of transmitting electrical energy from an energy source to an electrical load without interconnecting wires. An electrical transformer is the simplest instance of wireless energy transfer. The primary and secondary circuits of a transformer are not directly connected and the transfer of energy takes place by electromagnetic coupling through a process known as mutual induction. Power also may be transferred wirelessly using RF energy. Wireless power transfer technology using RF energy is produced by Powercast, Inc. and can achieve an output of 6 volts for a little over one meter. Other low-power wireless power technology has been proposed such as described in U.S. Pat. No. 6,967,462.

The apparatuses, systems, and methods in accordance with the described embodiments may be configured for minimally invasive ablation treatment of undesirable tissue through the use of irreversible electroporation to be able to ablate undesirable tissue in a controlled and focused manner without inducing thermally damaging effects to the surrounding healthy tissue. The apparatuses, systems, and methods in accordance with the described embodiments may be configured to ablate undesirable tissue through the use of electroporation or electropermeabilization. More specifically, the apparatuses, systems, and methods in accordance with the described embodiments may be configured to ablate undesirable tissue through the use of irreversible electroporation. Electroporation increases the permeabilization of a cell membrane by exposing the cell to electric pulses. The external electric field (electric potential/per unit length) to which the cell membrane is exposed to significantly increases the electrical conductivity and permeability of the plasma in the cell membrane. The primary parameter affecting the transmembrane potential is the potential difference across the cell membrane. Irreversible electroporation is the application of an electric field of a specific magnitude and duration to a cell membrane such that the permeabilization of the cell membrane cannot be reversed, leading to cell death without inducing a significant amount of heat in the cell membrane. The destabilizing potential forms pores in the cell membrane when the potential across the cell membrane exceeds its dielectric strength causing the cell to die under a process known as apoptosis and/or necrosis. The application of irreversible electroporation pulses to cells is an effective way for ablating large volumes of undesirable tissue without deleterious thermal effects to the surrounding healthy tissue associated with thermal-inducing ablation treatments. This is because irreversible electroporation destroys cells without heat and thus does not destroy the cellular support structure or regional vasculature. A destabilizing irreversible electroporation pulse, suitable to cause cell death without inducing a significant amount of thermal damage to the surrounding healthy tissue, may have amplitude in the range of about several hundred to about several thousand volts and is generally applied across biological membranes over a distance of about several millimeters, for example, for a relatively long duration. Thus, the undesirable tissue may be ablated in-vivo through the delivery of destabilizing electric fields by quickly creating cell necrosis.

The apparatuses, systems, and methods for electrical ablation therapy in accordance with the described embodiments may be adapted for use in minimally invasive surgical procedures to access the tissue treatment region in various anatomic locations such as the brain, lungs, breast, liver, gall bladder, pancreas, prostate gland, and various internal body lumen defined by the esophagus, stomach, intestine, colon, arteries, veins, anus, vagina, cervix, fallopian tubes, and the peritoneal cavity, for example, without limitation. Minimally invasive electrical ablation devices may be introduced to the tissue treatment region using a trocar inserted though a small opening formed in the patient's body or through a natural body orifice such as the mouth, anus, or vagina using translumenal access techniques known as Natural Orifice Translumenal Endoscopic Surgery (NOTES)™. Once the electrical ablation devices (e.g., electrodes) are located into or proximal to the undesirable tissue in the treatment region, electric field potentials can be applied to the undesirable tissue by the energy source. The electrical ablation devices comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or working channels of the endoscope, through small incisions, or transcutaneously (e.g., where electric pulses are delivered to the tissue treatment region through the skin).

FIG. 1 illustrates one embodiment of an electrical ablation system 10. The electrical ablation system 10 may be employed to ablate undesirable tissue such as diseased tissues, cancers, tumors, masses, lesions, abnormal tissue growths inside a patient using electrical energy. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, or any combinations thereof without limitation. The electrical ablation system 10 may be configured to be positioned within a natural body orifice of the patient such as the mouth, anus, or vagina and advanced through internal body lumen or cavities such as the esophagus, colon, cervix, urethra, for example, to reach the tissue treatment region. The electrical ablation system 10 also may be configured to be positioned and passed through a small incision or keyhole formed through the skin or abdominal wall of the patient to reach the tissue treatment region using a trocar. The tissue treatment region may be located in the brain, lungs, breast, liver, gall bladder, pancreas, prostate gland, various internal body lumen defined by the esophagus, stomach, intestine, colon, arteries, veins, anus, vagina, cervix, fallopian tubes, and the peritoneal cavity, for example, without limitation. The electrical ablation system 10 can be configured to treat a number of lesions and ostepathologies comprising metastatic lesions, tumors, fractures, infected sites, inflamed sites. Once positioned into or proximate the tissue treatment region, the electrical ablation system 10 can be actuated (e.g., energized) to ablate the undesirable tissue. In one embodiment, the electrical ablation system 10 may be configured to treat diseased tissue in the gastrointestinal (GI) tract, esophagus, lung, or stomach that may be accessed orally. In another embodiment, the electrical ablation system 10 may be adapted to treat undesirable tissue in the liver or other organs that may be accessible using translumenal access techniques such as, without limitation, NOTES™ techniques, where the electrical ablation devices may be initially introduced through a natural orifice such as the mouth, anus, or vagina and then advanced to the tissue treatment site by puncturing the walls of internal body lumen such as the stomach, intestines, colon, cervix. In various embodiments, the electrical ablation system 10 may be adapted to treat undesirable tissue in the brain, liver, breast, gall bladder, pancreas, or prostate gland, using one or more electrodes positioned percutaneously, transcutaneously, translumenally, minimally invasively, and/or through open surgical techniques, or any combination thereof.

In one embodiment, the electrical ablation system 10 may be employed in conjunction with a flexible endoscope 12, as well as a rigid endoscope, laparoscope, or thoracoscope, such as the GIF-100 model available from Olympus Corporation. In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrical ablation system 10 may be inserted and guided into or proximate the tissue treatment region using the endoscope 12.

In the embodiment illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more working channels for receiving various instruments, such as electrical ablation devices, for example, therethrough. Images within the field of view of the viewing port are received by an optical device, such as a camera comprising a charge coupled device (CCD) usually located within the endoscope 12, and are transmitted to a display monitor (not shown) outside the patient.

In one embodiment, the electrical ablation system 10 may comprise an electrical ablation device 20, a plurality of electrical conductors 18, a handpiece 16 comprising an activation switch 62, and an energy source 14, such as an electrical waveform generator, electrically coupled to the activation switch 62 and the electrical ablation device 20. The electrical ablation device 20 comprises a relatively flexible member or shaft 22 that may be introduced to the tissue treatment region using a variety of known techniques such as an open incision and a trocar, through one or more of the working channels of the endoscope 12, percutaneously, or transcutaneously.

In one embodiment, one or more electrodes (e.g., needle electrodes, balloon electrodes), such as first and second electrodes 24*a,b*, extend out from the distal end of the electrical ablation device 20. In one embodiment, the first electrode 24*a* may be configured as the positive electrode and the second electrode 24*b* may be configured as the negative electrode. The first electrode 24*a* is electrically connected to a first electrical conductor 18*a*, or similar electrically conductive lead or wire, which is coupled to the positive terminal of the energy source 14 through the activation switch 62. The second electrode 24*b* is electrically connected to a second electrical conductor 18*b*, or similar electrically conductive lead or wire, which is coupled to the negative terminal of the energy source 14 through the activation switch 62. The electrical conductors 18*a,b* are electrically insulated from each other and surrounding structures, except for the electrical connections to the respective electrodes 24*a,b*. In various embodiments, the electrical ablation device 20 may be configured to be introduced into or proximate the tissue treatment region using the endoscope 12 (laparoscope or thoracoscope), open surgical procedures, or external and non-invasive medical procedures. The electrodes 24*a,b* may be referred to herein as endoscopic or laparoscopic electrodes, although variations thereof may be inserted transcutaneously or percutaneously. As previously discussed, either one or both electrodes 24*a,b* may be adapted and configured to slideably move in and out of a cannula, lumen, or channel defined within the flexible shaft 22.

Once the electrodes 24*a,b* are positioned at the desired location into or proximate the tissue treatment region, the electrodes 24*a,b* may be connected to or disconnected from the energy source 14 by actuating or de-actuating the switch 62 on the handpiece 16. The switch 62 may be operated manually or may be mounted on a foot switch (not shown), for example. The electrodes 24*a,b* deliver electric field pulses to the undesirable tissue. The electric field pulses may be characterized based on various parameters such as pulse shape, amplitude, frequency, and duration. The electric field pulses may be sufficient to induce irreversible electroporation in the undesirable tissue. The induced potential depends on a variety of conditions such as tissue type, cell size, and electrical pulse parameters. The primary electrical pulse parameter affecting the transmembrane potential for a specific tissue type is the amplitude of the electric field and pulse length that the tissue is exposed to.

In one embodiment, a protective sleeve or sheath 26 may be slidably disposed over the flexible shaft 22 and within a handle 28. In another embodiment, the sheath 26 may be slidably disposed within the flexible shaft 22 and the handle 28, without limitation. The sheath 26 is slideable and may be located over the electrodes 24*a,b* to protect the trocar and prevent accidental piercing when the electrical ablation device 20 is advanced therethrough. Either one or both of the electrodes 24*a,b* of the electrical ablation device 20 may be adapted and configured to slideably move in and out of a cannula, lumen, or channel formed within the flexible shaft 22. The second electrode 24*b* may be fixed in place. The second electrode 24*b* may provide a pivot about which the first electrode 24*a* can be moved in an arc to other points in the tissue treatment region to treat larger portions of the diseased tissue that cannot be treated by fixing the electrodes 24*a,b* in one location. In one embodiment, either one or both of the electrodes 24*a,b* may be adapted and configured to slideably move in and out of a working channel formed within a flexible shaft 32 of the flexible endoscope 12 or may be located independently of the flexible endoscope 12. Various features of the first and second electrodes 24*a,b* are described in more detail in FIGS. 2A-D.

In one embodiment, the first and second electrical conductors 18*a,b* may be provided through the handle 28. In the illustrated embodiment, the first electrode 24*a* can be slideably moved in and out of the distal end of the flexible shaft 22 using a slide member 30 to retract and/or advance the first electrode 24*a*. In various embodiments either or both electrodes 24*a,b* may be coupled to the slide member 30, or additional slide members, to advance and retract the electrodes 24a,b, e.g., position the electrodes 24a,b. In the illustrated embodiment, the first electrical conductor 18a coupled to the first electrode 24a is coupled to the slide member 30. In this manner, the first electrode 24a, which is slidably movable within the cannula, lumen, or channel defined by the flexible shaft 22, can advanced and retracted with the slide member 30.

In various other embodiments, transducers or sensors 29 may be located in the handle 28 of the electrical ablation device 20 to sense the force with which the electrodes 24a,b penetrate the tissue in the tissue treatment zone. This feedback information may be useful to determine whether either one or both of the electrodes 24a,b have been properly inserted in the tissue treatment region. As is particularly well known, cancerous tumor tissue tends to be denser than healthy tissue and thus greater force is required to insert the electrodes 24a,b therein. The transducers or sensors 29 can provide feedback to the operator, surgeon, or clinician to physically sense when the electrodes 24a,b are placed within the cancerous tumor. The feedback information provided by the transducers or sensors 29 may be processed and displayed by circuits located either internally or externally to the energy source 14. The sensor 29 readings may be employed to determine whether the electrodes 24a,b have been properly located within the cancerous tumor thereby assuring that a suitable margin of error has been achieved in locating the electrodes 24a,b.

In one embodiment, the input to the energy source 14 may be connected to a commercial power supply by way of a plug (not shown). The output of the energy source 14 is coupled to the electrodes 24a,b, which may be energized using the activation switch 62 on the handpiece 16, or in one embodiment, an activation switch mounted on a foot activated pedal (not shown). The energy source 14 may be configured to produce electrical energy suitable for electrical ablation, as described in more detail below.

In one embodiment, the electrodes 24a,b are adapted and configured to electrically couple to the energy source 14 (e.g., generator, waveform generator). Once electrical energy is coupled to the electrodes 24a,b, an electric field is formed at a distal end of the electrodes 24a,b. The energy source 14 may be configured to generate electric pulses at a predetermined frequency, amplitude, pulse length, and/or polarity that are suitable to induce irreversible electroporation to ablate substantial volumes of undesirable tissue in the treatment region. For example, the energy source 14 may be configured to deliver DC electric pulses having a predetermined frequency, amplitude, pulse length, and/or polarity suitable to induce irreversible electroporation to ablate substantial volumes of undesirable tissue in the treatment region. The DC pulses may be positive or negative relative to a particular reference polarity. The polarity of the DC pulses may be reversed or inverted from positive-to-negative or negative-to-positive a predetermined number of times to induce irreversible electroporation to ablate substantial volumes of undesirable tissue in the treatment region.

In one embodiment, a timing circuit may be coupled to the output of the energy source 14 to generate electric pulses. The timing circuit may comprise one or more suitable switching elements to produce the electric pulses. For example, the energy source 14 may produce a series of n electric pulses (where n is any positive integer) of sufficient amplitude and duration to induce irreversible electroporation suitable for tissue ablation when the n electric pulses are applied to the electrodes 24a,b. In one embodiment, the electric pulses may have a fixed or variable pulse length, amplitude, and/or frequency.

The electrical ablation device 20 may be operated either in bipolar or monopolar mode. In bipolar mode, the first electrode 24a is electrically connected to a first polarity and the second electrode 24b is electrically connected to the opposite polarity. For example, in monopolar mode, the first electrode 24a is coupled to a prescribed voltage and the second electrode 24b is set to ground. In the illustrated embodiment, the energy source 14 may be configured to operate in either the bipolar or monopolar modes with the electrical ablation system 10. In bipolar mode, the first electrode 24a is electrically connected to a prescribed voltage of one polarity and the second electrode 24b is electrically connected to a prescribed voltage of the opposite polarity. When more than two electrodes are used, the polarity of the electrodes may be alternated so that any two adjacent electrodes may have either the same or opposite polarities, for example.

In monopolar mode, it is not necessary that the patient be grounded with a grounding pad. Since a monopolar energy source 14 is typically constructed to operate upon sensing a ground pad connection to the patient, the negative electrode of the energy source 14 may be coupled to an impedance simulation circuit. In this manner, the impedance circuit simulates a connection to the ground pad and thus is able to activate the energy source 14. It will be appreciated that in monopolar mode, the impedance circuit can be electrically connected in series with either one of the electrodes 24a,b that would otherwise be attached to a grounding pad.

In one embodiment, the energy source 14 may be configured to produce RF waveforms at predetermined frequencies, amplitudes, pulse widths or durations, and/or polarities suitable for electrical ablation of cells in the tissue treatment region. One example of a suitable RF energy source is a commercially available conventional, bipolar/monopolar electrosurgical RF generator such as Model Number ICC 350, available from Erbe, GmbH.

In one embodiment, the energy source 14 may be configured to produce destabilizing electrical potentials (e.g., fields) suitable to induce irreversible electroporation. The destabilizing electrical potentials may be in the form of bipolar/monopolar DC electric pulses suitable for inducing irreversible electroporation to ablate tissue undesirable tissue with the electrical ablation device 20. A commercially available energy source suitable for generating irreversible electroporation electric filed pulses in bipolar or monopolar mode is a pulsed DC generator such as Model Number ECM 830, available from BTX Molecular Delivery Systems Boston, Mass. In bipolar mode, the first electrode 24a may be electrically coupled to a first polarity and the second electrode 24b may be electrically coupled to a second (e.g., opposite) polarity of the energy source 14. Bipolar/monopolar DC electric pulses may be produced at a variety of frequencies, amplitudes, pulse lengths, and/or polarities. Unlike RF ablation systems, however, which require high power and energy levels delivered into the tissue to heat and thermally destroy the tissue, irreversible electroporation requires very little energy input into the tissue to kill the undesirable tissue without the detrimental thermal effects because with irreversible electroporation the cells are destroyed by electric field potentials rather than heat.

In one embodiment, the energy source 14 may be coupled to the first and second electrodes 24a,b by either a wired or a wireless connection. In a wired connection, the energy source 14 is coupled to the electrodes 24a,b by way of the electrical conductors 18a,b, as shown. In a wireless connection, the electrical conductors 18a,b may be replaced with a first antenna (not shown) coupled the energy source 14 and a second antenna (not shown) coupled to the electrodes 24a,b, wherein the second antenna is remotely located from the first antenna. In one embodiment, the energy source may comprise a wireless transmitter to deliver energy to the electrodes using wireless energy transfer techniques via one or more remotely positioned antennas. As previously discussed, wireless energy transfer or wireless power transmission is the process of transmitting electrical energy from the energy source 14 to an electrical load, e.g., the abnormal cells in the tissue treatment region, without using the interconnecting electrical conductors 18a,b. An electrical transformer is the simplest instance of wireless energy transfer. The primary and secondary circuits of a transformer are not directly connected. The transfer of energy takes place by electromagnetic coupling through a process known as mutual induction. Wireless power transfer technology using RF energy is produced by Powercast, Inc. The Powercast system can achieve a maximum output of 6 volts for a little over one meter. Other low-power wireless power technology has been proposed such as described in U.S. Pat. No. 6,967,462.

In one embodiment, the energy source 14 may be configured to produce DC electric pulses at frequencies in the range of about 1 Hz to about 10000 Hz, amplitudes in the range of about ±100 to about ±3000 VDC, and pulse lengths (e.g., pulse width, pulse duration) in the range of about 1 μs to about 100 ms. The polarity of the electric potentials coupled to the electrodes 24a,b may be reversed during the electrical ablation therapy. For example, initially, the DC electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 to about +1500 VDC, and pulse lengths of about 10 μs to about 50 μs. In another embodiment, the abnormal cells in the tissue treatment region may be electrically ablated with an electrical waveform having an amplitude of about +500 VDC and pulse duration of about 20 ms delivered at a pulse period T or repetition rate, frequency f=1/T, of about 10 Hz. It has been determined that an electric field strength of 1,000V/cm is suitable for destroying living tissue by inducing irreversible electroporation.

Figure 2A:
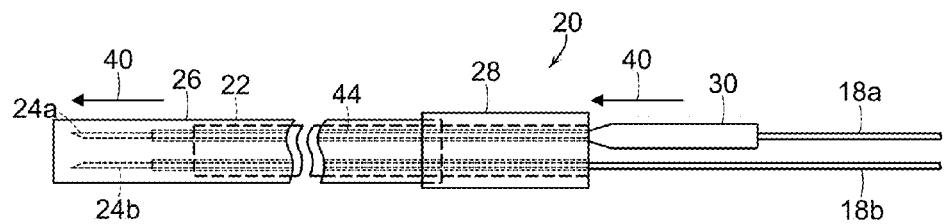
FIG. 2E illustrates one embodiment of the electrical ablation device comprising multiple needle electrodes.
Figure 2B:
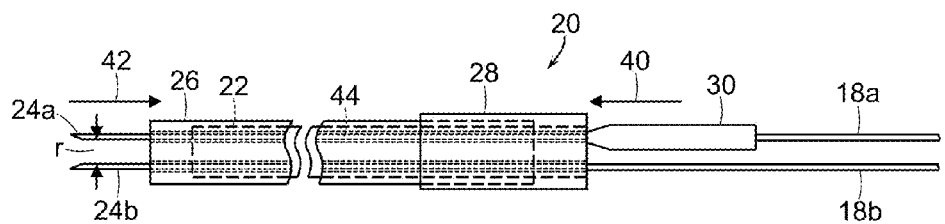
Figure 2C:
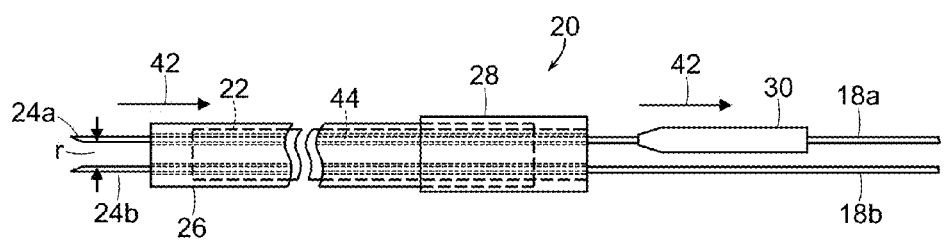
Figure 2D:
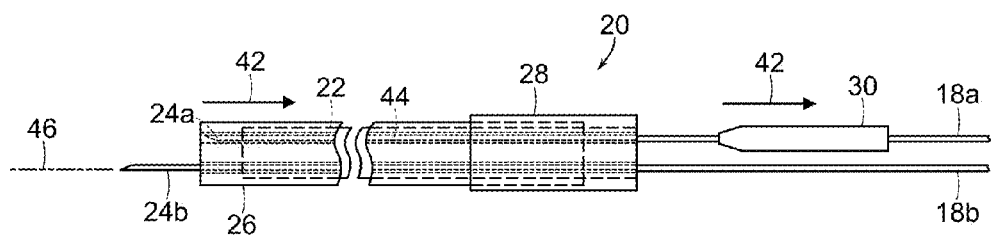
Figure 3:
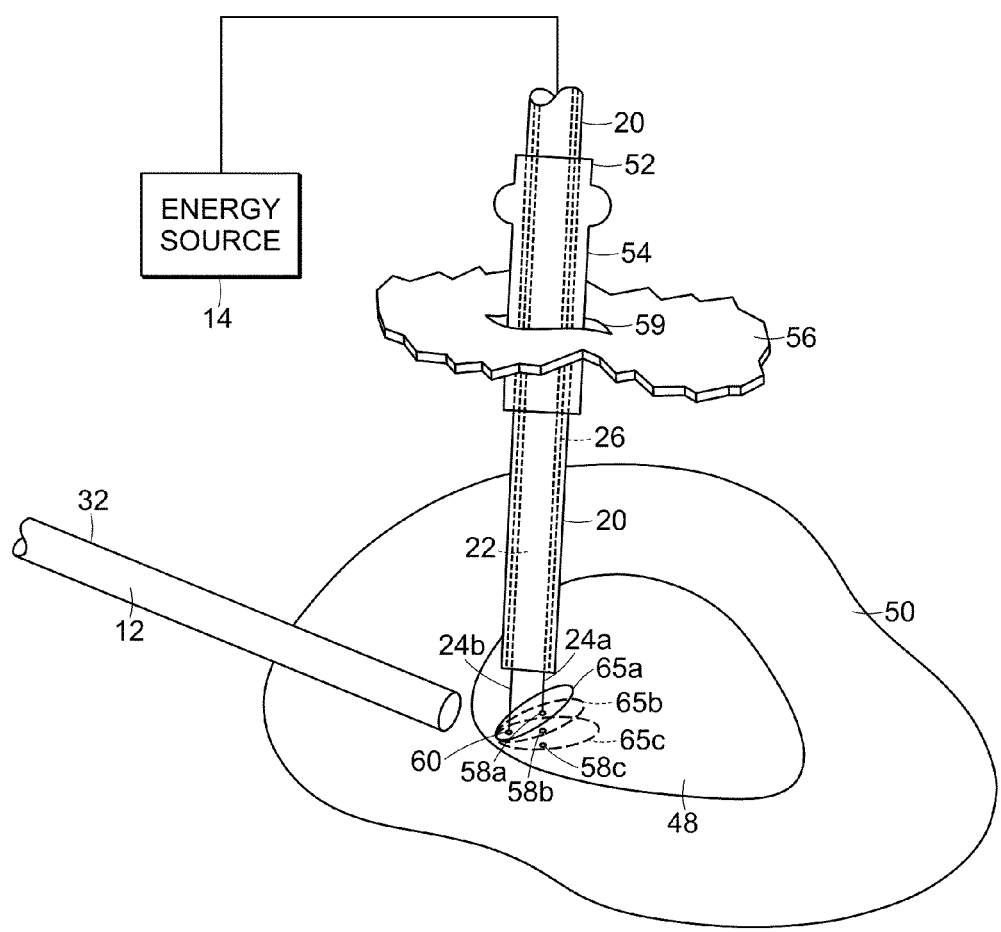
FIG. 3 illustrates one embodiment of the electrical ablation system shown in FIGS. 1 and 2A-D in use to treat undesirable tissue located on the surface of the liver.

FIGS. 2A-D illustrate one embodiment of the electrical ablation device 20 in various phases of deployment. In the embodiment illustrated in FIGS. 2A-D, the sheath 26 is disposed over the flexible shaft 22, however, those skilled in the art will appreciate that the sheath 26 may be disposed within the flexible shaft 22. The electrical ablation device 20 may be used in conjunction with the electrical ablation system 10 shown in FIG. 1. It will be appreciated that other devices and electrode configurations may be employed without limitation. FIG. 2A illustrates an initial phase of deployment wherein the sheath 26 is extended in the direction indicated by arrow 40 to cover the electrodes 24a,b. The electrodes 24a,b may have dimensions of about 0.5 mm, about 1 mm, or about 1.5 mm in diameter. It will be appreciated that the dimensions of the electrodes 24a,b may be anywhere from about 0.5 mm to about 1.5 mm in diameter. The electrical ablation device 20 may be introduced into the tissue treatment region through a trocar, as illustrated in FIG. 3, for example. FIG. 2B illustrates another phase of deployment wherein the sheath 26 is retracted within the handle 28 in the direction indicated by arrow 42. In this phase of deployment, the first and second electrodes 24a,b extend through the distal end of the flexible shaft 22 and are ready to be inserted into or proximate the tissue treatment region. The first electrode 24a may be retracted in direction 42 through a lumen 44 formed in the flexible shaft 22 by holding the handle 28 and pulling on the slide member 30. FIG. 2C illustrates a transition phase wherein the first electrode 24a is the process of being retracted in direction 42 by pulling on the slide member 30 handle, for example, in the same direction. FIG. 2D illustrates another phase of deployment wherein the first electrode 24a is in a fully retracted position. In this phase of deployment the electrical ablation device 20 can be pivotally rotated about an axis 46 defined by the second electrode 24b. The electrodes 24a,b are spaced apart by a distance "r." The distance "r" between the electrodes 24a,b may be 5.0 mm, about 7.5 mm, or about 10 mm. It will be appreciated that the distance "r" between the electrodes 24a,b may be anywhere from about 5.0 mm to about 10.0 mm. Thus, the electrical ablation device 20 may be rotated in an arc about the pivot formed by the second electrode 24b, the first electrode 24a may be placed in a new location in the tissue treatment region within the radius "r." Retracting the first electrode 24a and pivoting about the second electrode 24b enables the surgeon or clinician to target and treat a larger tissue treatment region essentially comprising a circular region having a radius "r," which is the distance between the electrodes 24a,b. Thus, the electrodes 24a,b may be located in a plurality of positions in and around the tissue treatment region in order to treat much larger regions of tissue. Increasing the electrode 24a,b diameter and spacing the electrodes 24a,b further apart enables the generation of an electric field over a much larger tissue regions and thus the ablation of larger volumes of undesirable tissue. In this manner, the operator can treat a larger tissue treatment region comprising cancerous lesions, polyps, or tumors, for example.

Although the electrical ablation electrodes according to the described embodiments have been described in terms of the particular needle type electrodes 24a,b as shown and described in FIGS. 1 and 2A-D, those skilled in the art will appreciate that other configurations of electrical ablation electrodes may be employed for the ablation of undesirable tissue, without limitation. In one embodiment, the electrical ablation device 20 may comprise two or more fixed electrodes that are non-retractable. In another embodiment, the electrical ablation device 20 may comprise two or more retractable electrodes, one embodiment of which is described below with reference to FIG. 2E. In another embodiment, the electrical ablation device 20 may comprise at least one slidable electrode disposed within at least one working channel of the flexible shaft 32 of the endoscope 12. In another embodiment, the electrical ablation device 20 may comprise at least one electrode may be configured to be inserted into the tissue treatment region transcutaneously or percutaneously. Still in various other embodiments, the electrical ablation device 20 may comprise at least one electrode configured to be introduced to the tissue treatment region transcutaneously or percutaneously and at least one other electrode may be configured to be introduced to the tissue treatment region through at least one working channel of the flexible shaft 32 of the endoscope 12. The embodiments, however, are not limited in this context.

Figure 2E:
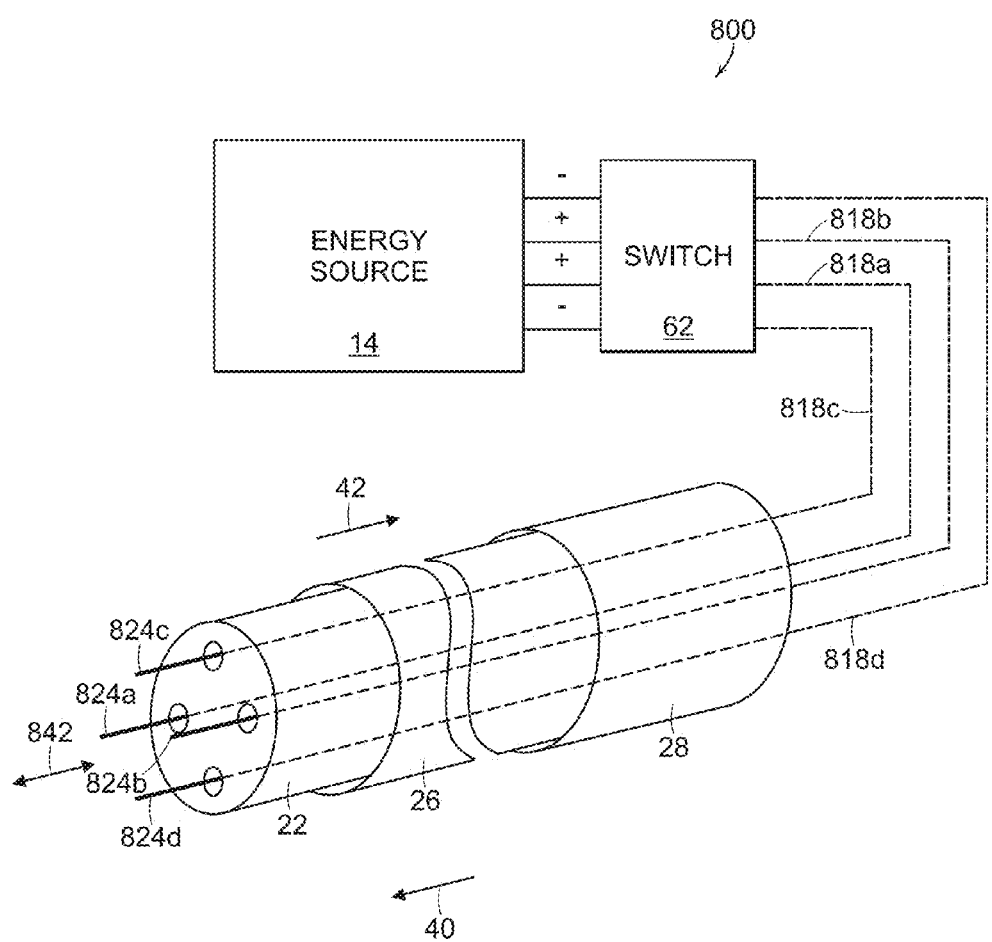

FIG. 2E illustrates one embodiment of an electrical ablation device 800 comprising multiple needle electrodes 824m, where m is any positive integer. In the illustrated embodiment, the electrical ablation device 800 comprises four electrodes 824a, 824b, 824c, 824d. It will be appreciated that in one embodiment, the electrical ablation device 800 also may comprise three needle electrodes 824a, 824b, 824c, without limitation. The electrical ablation device 800 may be used in conjunction with the electrical ablation system 10 shown in FIG. 1. It will be appreciated that other devices and electrode configurations may be employed without limitation. The electrodes 824a-m each may have dimensions of about 0.5 mm, about 1 mm, or about 1.5 mm in diameter. It will be appreciated that the dimensions of each of the electrodes 824a-m may be anywhere from about 0.5 mm to about 1.5 mm in diameter. The electrical ablation device 800 may be introduced into the tissue treatment region through a trocar, as subsequently described and illustrated with reference to FIG. 3, for example.

The electrical ablation device 800 comprises essentially the same components as the electrical ablation device 20 described with reference to FIGS. 2A-D. The electrical ablation device 800 comprises the relatively flexible member or shaft 22, the protective sheath 26, and one or more handles 28 to operate either the sheath 26, the electrodes 824a,b,c,d, or both. The electrodes 824a,b,c,d may be individually or simultaneously deployable and/or retractable in the direction indicated by arrow 842. The electrodes 824a,b,c,d extend out from the distal end of the electrical ablation device 800. In one embodiment, the first and second electrodes 824a, 824b may be configured as the positive electrode coupled to the anode of the energy source 14 via corresponding first and second electrical conductors 818a, 818b, and the third and fourth 824c, 824d may be configured as the negative electrode coupled to the cathode of the energy source 14 via corresponding third and fourth electrical conductors 818c, 818d, or similar electrically conductive leads or wires, through the activation switch 62. Once the electrodes 824a,b,c,d are positioned at the desired location into or proximate the tissue treatment region, the electrodes 824a,b,c,d may be connected/disconnected from the energy source 14 by actuating/de-actuating the switch 62.

As previously discussed with reference to FIGS. 2A-D, as shown in FIG. 2E in one embodiment, the protective sleeve or sheath 26 may be slidably disposed over the flexible shaft 22 and within the handle 28. In an initial phase of deployment, the sheath 26 is extended in direction 40 to cover the electrodes 824a,b,c,d to protect the trocar and prevent accidental piercing when the electrical ablation device 800 is advanced therethrough. Once the electrodes 824a,b,c,d are located into or proximate the tissue treatment region, the sheath 26 is refracted in direction 42 to expose the electrodes 824a,b,c,d. One or more of the electrodes 824a,b,c,d of the electrical ablation device 800 may be adapted and configured to slideably move in and out of a cannula, lumen, or channel formed within the flexible shaft 22. In one embodiment all of the electrodes 824a,b,c,d are configured to slideably move in and out channels formed within lumens formed within the flexible shaft 22, referred to for example as the lumen 44 in FIGS. 2A-D, to advance and retract the electrodes 824a,b,c,d as may be desired by the operator. Nevertheless, in other embodiments, it may be desired to fix all or certain ones of the one or more electrodes 824a,b,c,d in place.

The various embodiments of electrodes described in the present specification, e.g., the electrodes 24a,b, or 824a-m, may be configured for use with an electrical ablation device (not shown) comprising an elongated flexible shaft to house the needle electrodes 24a,b, or 824a-m, for example. The needle electrodes 24a,b, or 824a-m, are free to extend past a distal end of the electrical ablation device. The flexible shaft comprises multiple lumen formed therein to slidably receive the needle electrodes 24a,b, or 824a-m. A flexible sheath extends longitudinally from a handle portion to the distal end. The handle portion comprises multiple slide members received in respective slots defining respective walls. The slide members are coupled to the respective needle electrodes 24a,b, or 824a-m. The slide members are movable to advance and retract the electrode 24a,b, or 824a-m. The needle electrodes 24a,b, or 824a-m, may be independently movable by way of the respective slide members. The needle electrodes 24a,b, or 824a-m, may be deployed independently or simultaneously. An electrical ablation device (not shown) comprising an elongated flexible shaft to house multiple needle electrodes and a suitable handle is described with reference to FIGS. 4-10 in commonly owned U.S. patent application Ser. No. 11/897,676 titled ELECTRICAL ABLATION SURGICAL INSTRUMENTS, filed Aug. 31, 2007, now U.S. Patent Application Publication No. 2009/0062788, the entire disclosure of which is incorporated herein by reference in its entirety.

It will be appreciated that the electrical ablation devices 20, 800 described with referenced to FIGS. 2A-E, may be introduced inside a patient endoscopically (as shown in FIG. 15, transcutaneously, percutaneously, through an open incision, through a trocar (as shown in FIG. 3), through a natural orifice (as shown in FIG. 15), or any combination thereof. In one embodiment, the outside diameter of the electrical ablation devices 20, 800 may be sized to fit within a working channel of an endoscope and in other embodiments the outside diameter of the electrical ablation devices 20, 800 may be sized to fit within a hollow outer sleeve 620, or trocar, as shown in FIG. 15, for example. The hollow outer sleeve 620 or trocar is inserted into the upper gastrointestinal tract of a patient and may be sized to also receive a flexible endoscopic portion of an endoscope 622 (e.g., gastroscope), similar to the endoscope 12 described in FIG. 1.

FIG. 3 illustrates one embodiment of the electrical ablation system 10 shown in FIGS. 1 and 2A-D in use to treat undesirable tissue 48 located on the surface of the liver 50. The undesirable tissue 48 may be representative of a variety of diseased tissues, cancers, tumors, masses, lesions, abnormal tissue growths, for example. In use, the electrical ablation device 20 may be introduced into or proximate the tissue treatment region through a port 52 of a trocar 54. The trocar 54 is introduced into the patient via a small incision 59 formed in the skin 56. The endoscope 12 may be introduced into the patient trans-anally through the colon, trans-orally down the esophagus and through the stomach using translumenal techniques, or through a small incision or keyhole formed through the patient's abdominal wall (e.g., the peritoneal wall). The endoscope 12 may be employed to guide and locate the distal end of the electrical ablation device 20 into or proximate the undesirable tissue 48. Prior to introducing the flexible shaft 22 through the trocar 54, the sheath 26 is slid over the flexible shaft 22 in a direction toward the distal end thereof to cover the electrodes 24a,b (as shown in FIG. 2A) until the distal end of the electrical ablation device 20 reaches the undesirable tissue 48.

Once the electrical ablation device 20 has been suitably introduced into or proximate the undesirable tissue 48, the sheath 26 is retracted to expose the electrodes 24a,b (as shown in FIG. 2B) to treat the undesirable tissue 48. To ablate the undesirable tissue 48, the operator initially may locate the first electrode 24a at a first position 58a and the second electrode 24b at a second position 60 using endoscopic visualization and maintaining the undesirable tissue 48 within the field of view of the flexible endoscope 12. The first position 58a may be near a perimeter edge of the undesirable tissue 48. Once the electrodes 24a,b are located into or proximate the undesirable tissue 48, the electrodes 24a,b are energized with irreversible electroporation pulses to create a first necrotic zone 65a. For example, once the first and second electrodes 24a,b are located in the desired positions 60 and 58a, the undesirable tissue 48 may be exposed to an electric field generated by energizing the first and second electrodes 24a,b with the energy source 14. The electric field may have a magnitude, frequency, and pulse length suitable to induce irreversible electroporation in the undesirable tissue 48 within the first necrotic zone 65a. The size of the necrotic zone is substantially dependent on the size and separation of the electrodes 24a,b, as previously discussed. The treatment time is defined as the time that the electrodes 24a,b are activated or energized to generate the electric pulses suitable for inducing irreversible electroporation in the undesirable tissue 48.

This procedure may be repeated to destroy relatively larger portions of the undesirable tissue 48. The position 60 may be taken as a pivot point about which the first electrode 24a may be rotated in an arc of radius "r," the distance between the first and second electrodes 24a,b. Prior to rotating about the second electrode 24b, the first electrode 24a is refracted by pulling on the slide member 30 (FIGS. 1 and 2A-D) in a direction toward the proximal end and rotating the electrical ablation device 20 about the pivot point formed at position 60 by the second electrode 24b. Once the first electrode 24a is rotated to a second position 58b, it is advanced to engage the undesirable tissue 48 at point 58b by pushing on the slide member 30 in a direction towards the distal end. A second necrotic zone 65b is formed upon energizing the first and second electrodes 24a,b. A third necrotic zone 65c is formed by retracting the first electrode 24a, pivoting about pivot point 60 and rotating the first electrode 24a to a new location, advancing the first electrode 24a into the undesirable tissue 48 and energizing the first and second electrodes 24a,b. This process may be repeated as often as necessary to create any number of necrotic zones 65p, where p is any positive integer, within multiple circular areas of radius "r," for example, that is suitable to ablate the entire undesirable tissue 48 region. At anytime, the surgeon or clinician can reposition the first and second electrodes 24a,b and begin the process anew. In other embodiments, the electrical ablation device 800 comprising multiple needle electrodes 824a-m described with reference to FIG. 2E may be employed to treat the undesirable tissue 48. Those skilled in the art will appreciate that similar techniques may be employed to ablate any other undesirable tissues that may be accessible trans-anally through the colon, and/or orally through the esophagus and the stomach using translumenal access techniques. Therefore, the embodiments are not limited in this context.

Figure 4:
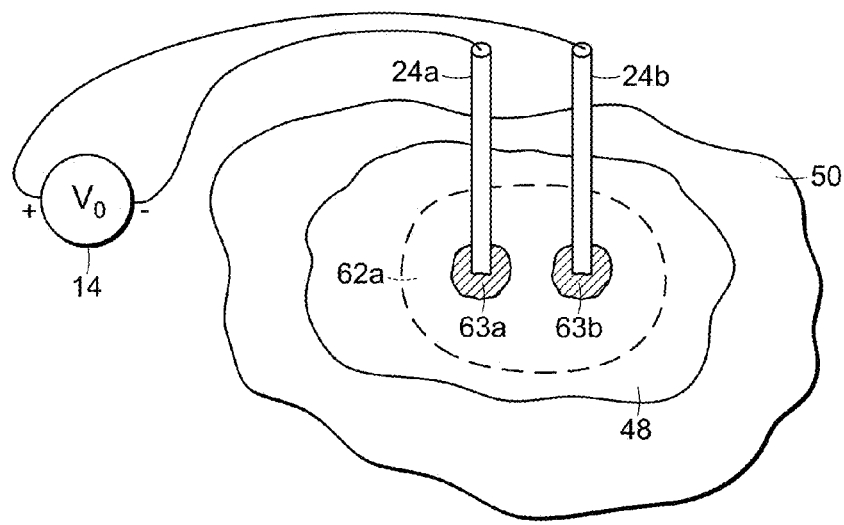
FIG. 4 illustrates a detailed view of one embodiment of the electrical ablation system shown in FIG. 3 in use to treat undesirable tissue located on the surface of the liver.

FIG. 4 illustrates a detailed view of one embodiment of the electrical ablation system 10 shown in FIG. 3 in use to treat undesirable tissue 48 located on the surface of the liver 50. The first and second electrodes 24a,b are embedded into or proximate the undesirable tissue 48 on the liver 50. The first and second electrodes 24a,b are energized to deliver one or more electrical pulses of amplitude and length sufficient to induce irreversible electroporation in the undesirable tissue 48 and create the first necrotic zone 65a. Additional electric pulses may be applied to the tissue immediately surrounding the respective electrodes 24a,b to form second, thermal, necrotic zones 63a,b near the electrode-tissue-interface. The duration of an irreversible electroporation energy pulse determines whether the temperature of the tissue 63a,b immediately surrounding the respective electrodes 24a,b raises to a level sufficient to create thermal necrosis. As previously discussed, varying the electrode 24a,b size and spacing can control the size and shape of irreversible electroporation induced necrotic zone 65a. Electric pulse amplitude and length can be varied to control the size and shape of the thermally induced necrotic zones near the tissue-electrode-interface. In other embodiments, the electrical ablation device 800 comprising multiple needle electrodes 824a-m may be used to treat the undesirable tissue 48 located on the surface of the liver 50, for example.

Figure 5:
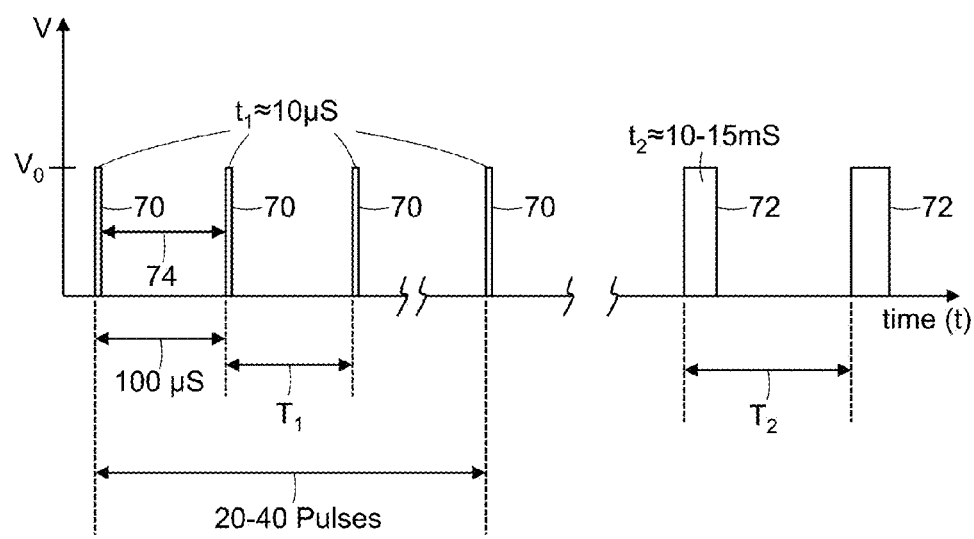
FIG. 5 is a graphical representation of a series of electrical pulses that may be applied to undesirable tissue to create a first necrotic zone by inducing irreversible electroporation in the tissue and to create a second necrotic zone by inducing thermal effects near the electrode-tissue-interface using the electrical ablation system shown in FIG. 4.

FIG. 5 is a graphical representation of a series of electrical pulses that may be applied to undesirable tissue to create a first necrotic zone by inducing irreversible electroporation in the tissue and to create a second necrotic zone by inducing thermal effects near the electrode-tissue-interface using the electrical ablation system 10 shown in FIG. 4. Time (t) is shown along the horizontal axis and voltage (VDC) is shown along the vertical axis. Initially the undesirable tissue 48 is exposed to a first series of electrical pulses 70 of a first predetermined amplitude, length, and frequency sufficient to induce the irreversible electroporation necrotic zone 65a. Subsequently, the undesirable tissue near the electrode-tissue-interface is exposed to a second series of electrical pulses 72 of a second predetermined amplitude, length, and frequency sufficient to induce thermal necrotic effects on the tissue and create thermal necrotic zones 63a,b. As shown in FIG. 5, the first series of pulses 70 comprises about 20 to 40 electric pulses having an amplitude of about 1000 VDC, pulse length $t_1$ of about 10 μs to about 15 μs, and a period $T_1$ (e.g., pulse repetition rate $f_1 = 1/T_1$) of about 100 μs ($f_1 = 10000$ Hz). The first series of pulses is sufficient to induce irreversible electroporation in the necrotic zone 65a. The period $T_1$ is defined as the pulse length $t_1$ plus the pulse spacing 74, e.g., the time between a falling edge of a pulse and a rising edge of a subsequent pulse. The second series of pulses 72 may comprises a single pulse or multiple pulses having an amplitude of about 500 VDC, pulse length $t_2$ of about 10 ms to about 15 ms, and a period $T_2$ of about 100 ms ($f_2 = 10$ Hz). The second series of pulses is sufficient to create thermal necrotic zones 63a,b in the tissue near the electrode-tissue-interface immediately surrounding the respective electrodes 24a,b. In one embodiment, $f_1 = f_2 = 10$ Hz (i.e., $T_1 = T_2 = 100$ MS).

In one embodiment, the thermal necrotic zones 63a,b formed in the tissue immediately surrounding the electrodes 24a,b at the tissue-electrode-interface are beneficial to stop bleeding in the undesirable tissue 48 as a result of the mechanical trauma resulting from inserting or embedding the electrodes 24a,b into the undesirable tissue 48 of the liver 50. Although in general irreversible electroporation induced by electric pulses do not cause thermal necrosis or other detrimental thermal effects, the longer electrical pulses 72 may be applied to the undesirable tissue 48 in succession to thermally seal the tissue immediately surrounding the electrodes 24a,b at the tissue-electrode-interface. Thus, the technique of applying a combination of a first series of substantially shorter electrical pulses 70 (in the microseconds range) and a second series of substantially longer energy pulses 72 (in the milliseconds range) may be employed for sealing vessels prior to transecting a vessel. Accordingly, the first series of pulses 70 may be applied to a vessel to induce cell necrosis by irreversible electroporation. Then, the second series of pulses 72 may be applied to vessel to create thermal necrotic zones to seal the vessel prior to dissecting the vessel.

In various embodiments, a series of electrical pulses may be characterized according to the following parameters as may be provided by the energy source 14, for example. In one embodiment, the energy source 14 may be configured to produce DC electric pulses at frequencies in the range of about 1 Hz to about 10000 Hz, amplitudes in the range of about ±100 to about ±3000 VDC, and pulse lengths (e.g., pulse width, pulse duration) in the range of about 1 µs to about 100 ms. The polarity of the electric potentials coupled to the electrodes 24a,b may be reversed during the electrical ablation therapy. For example, initially, the DC electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 to about +1500 VDC, and pulse lengths of about 10 µs to about 50 µs. In another embodiment, the abnormal cells in the tissue treatment region may be electrically ablated with an electrical waveform having an amplitude of about +500 VDC and pulse duration of about 20 ms delivered at a pulse period T or repetition rate, frequency f=1/T, of about 10 Hz.

FIGS. 6, 7, and 8 illustrate one embodiment of an electrical ablation device 290 to treat undesirable tissue located within body lumen using electrical energy. FIG. 6 illustrates a sectioned view of one embodiment of the electrical ablation device 290. FIG. 7 illustrates an end view of the embodiment of the electrical ablation device 290 shown in FIG. 6. FIG. 8 illustrates a cross-sectional view of the embodiment of the electrical ablation device 290 shown in FIG. 6. As previously discussed, reflux disease of the greater saphenous vein (GSV) can result in a varicose vessel 292, which is illustrated in FIG. 8. Conventionally, varicose veins have been treated by stripping and then applying either chemical or thermal ablation to internal portions of a lumen defined by the varicose vessel 292. In the embodiment illustrated in FIGS. 6-8, the electrical ablation device 290 is configured to couple to the energy source 14 and to be inserted within a lumen defined by the varicose vessel 292. Once inserted into the varicose vessel 292, the electrical ablation device 290 may be energized by the energy source 14 to apply high-voltage DC electrical pulses to an inner wall 294 portion of the varicose vessel 292. High-voltage DC pulses may be used to ablate the undesirable tissue and to subsequently seal the varicose vessel 292. The embodiment illustrated in FIGS. 6-8, however, is not limited in this context, and the electrical ablation device 290 may be employed to treat and seal tissue within any inner body lumen using energy in the form of electrical pulses supplied by the energy source 14.

Referring to FIGS. 6-8, the electrical ablation device 290 comprises a probe 296 comprising a cannula, channel, or lumen 300 extending longitudinally therethrough. The distal end 298 of the probe 296 comprises first and second ring electrodes 302a,b to which a potential difference may be applied by the energy source 14. The first and second ring electrodes 302a,b may be coupled to respective positive and negative terminals of the energy source 14 through corresponding first and second electrical conductors 304a,b. The first and second electrical conductors 304a,b extend through respective conduits 306a,b formed within the probe 296 and extend longitudinally therethrough. The first and second electrical conductors 304a,b may be electrically coupled to the first and second ring electrodes 302a,b in any suitable manner. The first and second ring electrodes 302a,b are adapted to receive energy in the form of electrical pulses from the energy source 14. The electrical pulses generate an electric field suitable for treating, e.g., ablating, the undesirable tissue within a lumen such as the lumen defined by the varicose vessel 292 as shown in FIG. 8. In one embodiment, once energized by the energy source 14, the first and second ring electrodes 302a,b generate an electric field suitable to induce irreversible electroporation in the undesirable tissue. It will be appreciated that a potential difference may be created across the first and second ring electrodes 302a,b to generate an electric field strength suitable to induce irreversible electroporation in the undesirable tissue. In other embodiments, the probe 296 may comprise one or more electrodes in addition to the first and second ring electrodes 302a,b.

The electrical ablation probe 296 has a form factor that is suitable to be inserted within a lumen defined by the varicose vessel 292 and to ablate tissue in the tapered lumen 298 portion of the varicose vessel 292. The probe 296 engages the inner wall 294 of the varicose vessel 292 in the tapered lumen 298 portion of the varicose vessel 292. Suction 306 applied at a proximal end of the probe 296 draws a vacuum within the lumen 300 of the probe 296 to collapse the varicose vessel 292 at the distal end 298 of the probe 296. Once the vessel 292 is collapsed or pulled down by the suction 306, a first pulse train 302 of high-voltage DC electrical pulses at a first amplitude $A_1$ (e.g., ~1000V amplitude) and a first pulse length $T_1$ (e.g., ~50 microseconds) is applied to the first and second ring electrodes 302a,b by the energy source 14. The high-voltage DC pulse train 302 eventually kills the cells within the tapered lumen 298 portion of the varicose vessel 292 by irreversible electroporation. A second pulse train 304 having a lower voltage amplitude $A_2$ (e.g., ~500 VDC) and a second longer pulse length $T_2$ (e.g., ~15 milliseconds) is applied to the first and second ring electrodes 302a,b of the probe 296 to thermally seal the varicose vessel 292. As previously discussed, in one embodiment, the polarity of the electrical pulses may be inverted or reversed by the energy source 14 during the ablation or sealing treatment process. In various embodiments, the electrical pulses may be characterized by the parameters in accordance with the output of the energy source 14 as discussed with respect to FIGS. 1 and 5, for example.

FIG. 9 illustrates one embodiment of an electrical ablation system 400 in use to treat non-metastatic prostate cancer in a patient. As previously discussed, a radical prostatectomy in which the entire prostate 404 and surrounding lymph nodes are removed is one of the conventional treatments for prostate cancer. Like most other forms of cancer, radiation therapy may be used in conjunction with or as an alternate method for the treatment of prostate cancer. Another thermal ablation technique for the treatment of prostate cancer is RF interstitial tumor ablation (RITA) via trans-rectal ultrasound guidance. While these conventional methods for the treatment of prostate cancer are effective, they are not preferred by many surgeons and may result in detrimental thermal effects to healthy tissue surrounding the prostate. The electrical ablation system 400 in accordance with the described embodiments provides improved electrical ablation of prostate cancer using irreversible electroporation pulses through supplied by an energy source to electrodes positioned into and/or proximate the prostrate cancer tissue.

With reference to FIG. 9, the electrical ablation system 400 comprises an electrical ablation device 402 comprising at least two electrodes 402a,b, and the energy source 14. The electrical ablation system 400 may be adapted for use in conjunction with the electrical ablation system 10 described in FIG. 1. The electrodes 402a,b are configured to be positioned within internal body lumens or cavities and, in one embodiment, may be configured for use in conjunction with the flexible endoscope 12 also described in FIG. 1. The electrodes 402a,b are configured to couple to the corresponding electrical conductors 18a,b, the handpiece 16, the activation switch 62, and the energy source 14, as previously discussed in FIG. 1. The first electrode 402a comprises a wire or flexible conductive tube that may be introduced through the urethra 406 into the prostate 404 proximally to the bladder 410. The first electrode 402a may be located into the prostate 404 using well known fluoroscopy or ultrasonic guidance, for example. The second electrode 402b comprises a pad and may be introduced into the anus 408 and advanced to a location proximate to the prostate 404. The first electrode 402a has a much smaller surface area relative to the trans-anally placed second electrode 402b pad. The first electrode 402a may be connected to the positive (+) terminal of the energy source 14 and the second electrode 402b may be connected to the negative (−) terminal of the energy source 14. In one embodiment, the energy source 14 may e configured as a high-voltage DC electric pulse generator. The activation switch 62 portion of the handpiece 16, as shown in FIG. 1, can be used to energize the electrical ablation system 400 to ablate the non-metastatic cancer in the prostrate 404 by irreversible electroporation pulses supplied by the energy source 14 and delivered through the electrodes 402a,b as described in FIG. 10 below. In other embodiments, the probe 296 may comprise one or more electrodes in addition to the first and second electrodes 402a,b.

FIG. 10 is a graphical representation of a series of electrical pulses 412 that may be applied to undesirable tissue to induce irreversible electroporation suitable to ablate non-metastatic cancer of the prostrate 404 as described in FIG. 9. Time (t) is shown along the horizontal axis and voltage (V) is shown along the vertical axis. A series of electrical pulses 412 having a predetermined amplitude $V_o$ and pulse length $t_o$ sufficient to induce irreversible electroporation may be applied to the prostate 404 through the electrodes 402a,b to ablate the undesirable cancerous tissue. Multiple electrical pulses 412, for example, 20 to 40 pulses, of amplitude of about 1500 to about 3000 volts DC ($V_o$) each having a pulse length $t_o$ of about 10 µs to about 50 µs, and a period (T) of about 10 ms. The electrical pulses 412 having such parameters are sufficient to induce irreversible electroporation to ablate the cancerous tissue in the prostate 404. The period T (e.g., pulse repetition rate f=1/T) may be defined as the pulse length $t_o$ plus 10 µs the length of time between pulses, or the pulse spacing 414. A conductive fluid may be introduced into the urethra 406 to extend the range of the positive electrode 402a. In various embodiments, the electrical pulses may be characterized by the parameters in accordance with the output of the energy source 14 as discussed with respect to FIGS. 1 and 5, for example.

FIG. 11 illustrates one embodiment of the electrical ablation system 10 described FIG. 1 in use to treat basal cell carcinoma (BCC) tissue. In FIG. 11, the electrical ablation system 10, described in FIG. 1, is shown in use to treat BCC tissue 502. BCC tissue 502 is a slowly growing cutaneous malignancy derived from a rapidly proliferating basal layer of the epidermis 504. As previously discussed, conventional treatments for BCC include surgical excision, cryotherapy, radiation, photodynamic therapy, Moh's micrographic surgery, and topical treatments with 5-fluorouracil. Minimally-invasive methods of treating BCC include laser ablation with a pulsed carbon dioxide laser. Although, the treatment of BCC with a carbon dioxide laser has been shown to be effective on tumors ranging in size from about 5 mm to about 40 mm, carbon dioxide treatment is a thermal method of treating tissue that may cause permanent thermal damage to healthy tissue surrounding the BCC tissue and requires costly capital investment in carbon dioxide laser equipment.

The electrical ablation device 20 of the electrical ablation system 10 may be used to induce irreversible electroporation suitable to treat undesirable BCC tissue using electrical pulses supplied by the energy source 14. The first and second electrodes 24a,b are transcutaneously inserted through the epidermis 504 and embedded into the BCC tissue 502. The first and second electrodes 24a,b are separated by a distance "D." The first electrode 24a is electrically to the positive (+) output of the energy source 14 and the second electrode 24b is electrically connected to the negative (−) output of the energy source 14. In one embodiment, the energy source 14 may be a high-voltage DC generator. The energized electrodes 24a,b generate an electric field inducing irreversible electroporation suitable for ablating the undesirable BCC tissue 502 located between the electrodes 24a,b. A larger portion of the BCC tissue 502 may be ablated by relocating and re-energizing the first and second electrodes 24a,b using the technique previously described with reference to FIG. 3, for example. As previously discussed, varying the electrode 24a,b size and spacing can control the size and shape of irreversible electroporation induced necrotic zone. Accordingly, as previously discussed, increasing the electrode 24a,b diameter and spacing between the electrodes 24a,b enables the generation of an electric field over a much larger tissue regions and thus the ablation of larger volumes of undesirable tissue. In other embodiments, the electrical ablation device 800 comprising multiple needle electrodes 824a-m may be used to treat the BCC tissue 502, for example.

FIG. 12 is a graphical representation of a series of electrical pulses 512 that may be applied to undesirable tissue to induce irreversible electroporation suitable to ablate BCC tissue as described in FIG. 11. Time (t) is shown along the horizontal axis and voltage (V) is shown along the vertical axis. As shown in FIG. 12, a series of electrical pulses 512 having a predetermined amplitude $V_o$ and pulse length $t_o$ sufficient to induce irreversible electroporation may be applied to the BCC tissue 502 to ablate the undesirable cancerous tissue. About 20 to about 40 pulses 512 of with an amplitude of about 1500 to about 3000 VDC ($V_o$), a pulse length $t_o$ of about 10 µs to about 50 µs, a period T (the pulse length $t_o$ plus the pulse spacing 54) of about 10 ms may be suitable for inducing irreversible electroporation to ablate the undesirable BCC tissue 502 in the region D between the electrodes 24a,b. Multiple placements of the electrode 24a,b in rapid succession and the application of additional pulses 512 can be used to ablate larger portions of the BCC tissue 502, as previously discussed in FIG. 3. As previously discussed, varying the electrode 24a,b size and spacing can control the size and shape of irreversible electroporation induced necrotic zone. Accordingly, increasing the electrode 24a,b diameter and spacing the electrodes 24a,b further apart (e.g., greater than "D") enables the generation of an electric field over a much larger tissue regions and thus the ablation of larger volumes of undesirable tissue. Injecting a conductive fluid into the BCC tissue 502 is another technique to increase the size and shape of the irreversible electroporation induced necrotic zone and extend the range of the positive electrode 24a, for example. In various embodiments, the electrical pulses may be characterized by the parameters in accordance with the output of the energy source 14 as discussed with respect to FIGS. 1 and 5, for example.

FIG. 13A illustrates one embodiment of an electrical ablation device 600 in a collapsed state. The electrical ablation device 600 has a configuration suitable for the treatment of undesirable tissue located in a lumen, abscess, void, or cavity. Although other electrode configurations may be effective for treating line-of-sight regions of tissue, such electrodes may not be as effective at treating tissue within a cavity. To overcome these limitations, the electrical ablation device 600 comprises an electrode configured to inflate and expand into the cavity to make contact with tissue along the inner wall of the cavity. The electrical ablation device 600 comprises an elongate tubular body extending from a proximal end to a distal end. In one embodiment, the electrical ablation device 600 may comprise a conductive elastomer electrode 602 portion (e.g., balloon, tip) and a non-conductive catheter 604 portion, which may be formed of a non-electrically conductive (e.g., electrically insulative) elastomeric material. The electrical ablation device 600 may be referred to as a balloon catheter, balloon probe, or balloon-tipped catheter, for example, without limitation. In one embodiment, the inflatable portion of the conductive elastomer electrode 602 may be formed of an electrically conductive elastomer suitable for coupling to the energy source 14 via an electrically conductive terminal 610 and a first electrically conductive wire 608a. Once inflated, the elastomeric properties of the conductive elastomer electrode 602 conform to the internal walls of the cavity. Upon energizing, the conductive elastomer electrode 602 delivers electrical pulses to the tissue within the internal walls of the cavity to induce irreversible electroporation.

In one embodiment, the electrical ablation device 600 may be fabricated using a concurrent injection process such that the conductive elastomer electrode 602 portion and the non-conductive catheter 604 portion are formally integrally. In another embodiment, the electrical ablation device 600 may be fabricated by manufacturing the conductive elastomer electrode 602 and the non-conductive catheter 604 separately and then joining the two components using any suitable joining method such as, for example, bolting, screwing, welding, crimping, gluing, bonding, brazing, soldering, press fitting, riveting, heat shrinking, heat welding, ultrasonic welding, or any other suitable method.

FIG. 13B illustrates one embodiment of the electrical ablation device 600 shown in FIG. 13A in an inflated state. As previously discussed, in an inflated state the conductive elastomer electrode 602 may be employed for ablating cancerous tumors growing within internal body lumens such as the esophagus or the large bowel, or in cavities remaining when cancerous tumors are removed from solid tissue, such as the breast. Although surgical resection of tumors in solid tissue can include a margin of healthy tissue, cancer cells may remain in the tissue within the cavity. The conductive elastomer electrode 602 may be inserted in the cavity, inflated, and energized by the energy source 14 to expose the tissue within the cavity to electrical pulses suitable to induce irreversible electroporation to ablate any cancer cells remaining within the cavity.

FIG. 14 is a cross-sectional view of the electrical ablation device 600 showing a cross-sectional view of the conductive elastomer electrode 602 and the non-conductive catheter 604 shown in FIGS. 13A and 13B. The conductive elastomer electrode 602 may be coupled to a first end 606 of the electrically conductive wire 608a. The wire 608a may be located through the non-conductive catheter 604 and the first end 606 electrically connected (e.g., bonded, soldered, brazed) to the conductive elastomer electrode 602 through the electrically conductive terminal 610. In one embodiment, the non-conductive catheter 604 may be extruded with an embedded strip of conductive material serving as the electrically conductive terminal 610. The wire 608a may be electrically connected to one end of the electrically conductive terminal 610. In one embodiment, the electrical ablation device 600 may be configured to couple to one terminal of the energy source 14 via a second end of the electrically conductive wire 608a. A return electrode 612 (e.g., in the form of a pad or needle electrode) is coupled to a second electrically conductive wire 608b, which is coupled to another terminal of the energy source 14. The return electrode 612 may be orientated proximal to the conductive elastomer electrode 602 of the electrical ablation device 600 (e.g., the balloon catheter). When irreversible electroporation energy pulses are applied to the conductive elastomer electrode 602 of the electrical ablation device 600, the tissue between the conductive elastomer portion 602 and the return electrode 608b is ablated, e.g., destroyed by the pulsed irreversible electroporation energy. In other embodiments, the return electrode 612 may comprise multiple electrodes, for example.

In one embodiment, the conductive elastomer electrode 602 may be fabricated from or may comprise an electrically conductive material suitable for conducting electrical energy from the energy source 14 to the internal cavity sufficient tot induce irreversible electroporation to the tissue within the cavity. The electrically conductive elastomer material is similar to conductive elastomers used as gasket material for electronic enclosures used for shielding electronic devices from electromagnetic interference (EMI). Conductive elastomers may be formed by infiltrating an elastomeric matrix with electrically conductive filler materials such as silver, gold, copper, or aluminum, to produce a hybrid material having the elastic properties of the elastomeric matrix and the electrically conductive properties of the metallic filler materials (some materials may have volume resistivity values as low as 0.004 $\Omega$-cm, for example). The conductive elastomer may be formed as thin sheets, catheters, and balloons suitable for medical applications. In one embodiment, the conductive elastomer electrode 602 may be fabricated from medical grade polyurethane material comprising at least one electrically conductive coating on an outer surface thereof. In another embodiment, the conductive elastomer electrode 602 may be made from an electrically conductive material. In yet another embodiment, the conductive elastomer electrode 602 may be made from an electrically insulative material, such as the medical grade polyurethane, and inflated with a conductive fluid (e.g., saline) to form the electrically conductive portion of the conductive elastomer electrode 602.

In one embodiment the conductive elastomer electrode 602 may be coupled to the anode (+) electrode of the energy source 14 and in another embodiment the conductive elastomer electrode 602 may be coupled to the cathode (−) electrode of the energy source 14. It will be appreciated that the polarity of the conductive elastomer electrode 602 may be reversed by reversing the output polarity of the energy source 14. In one embodiment, the conductive elastomer electrode 602 may be coupled to either the anode (+) or the cathode (−) of the energy source 14. For example, the conductive elastomer electrode 602 may be coupled to the cathode (+) of the energy source 14 relative to a ground plane cathode (−) in contact with the patient and coupled to the negative terminal of the energy source 14.

FIG. 15 illustrates one embodiment of the electrical ablation device shown in FIG. 13A inserted through the mouth and esophagus to ablate cancerous tissue in the esophagus using electrical pulses. As shown in FIG. 15, a hollow outer sleeve 620 or trocar is inserted into the upper gastrointestinal tract of a patient and receives a flexible endoscopic portion of an endoscope 622 (e.g., gastroscope), similar to the endoscope 12 described in FIG. 1. A variety of different types of endoscopes are known and, therefore, their specific construction and operation will not be discussed in great detail herein. In various embodiments, the flexible endoscopic portion 620 may be fabricated from nylon or high-density polyethylene plastic, for example. FIG. 15 illustrates, in general form, one embodiment of the electrical ablation device 600 that can be inserted through a natural orifice such as the mouth 626 and advanced through a cavity or lumen such as the esophagus 628, e.g., esophageal cavity, to apply electrical pulses sufficient to induce irreversible electroporation to ablate the undesirable cancerous tissue 630 located in the esophagus 628.

FIG. 16 illustrates the distal portion 624 of the endoscope 622 shown in FIG. 15. As shown in FIG. 16, the electrical ablation device 600 is advanced through the distal end 624 of the endoscope 622. In various embodiments, the endoscope 622 can serve to define various tool-receiving passages 628, or "working channels," that extend from the natural orifice 626 to the surgical site. In addition, the endoscope 622 comprises a viewing port 630. The endoscope 622 may be used for viewing the surgical site within the patient's body. Various cameras and/or lighting apparatuses may be inserted into the viewing port 630 of the endoscope 622 to provide the surgeon with a view of the surgical site.

With reference now to FIGS. 15 and 16, the electrical ablation device 600 is one of the tools or surgical instruments that can be accommodated in the tool-receiving passage 628 of the endoscope 622. The conductive elastomer electrode 602 (e.g., balloon, tip) and the non-conductive catheter 604 are configured to communicate with at least one pressurized air source 634 and a vacuum source 632 to respectively inflate and deflate the conductive elastomer electrode 602. In one embodiment, a vacuum/air tube 636 can be sized to receive other surgical instruments therein. In various embodiments, the endoscope 622 may comprise a video camera that communicates with a video display unit 638 that can be viewed by the surgeon during the operation. In addition, the endoscope 622 may further comprise a fluid-supply lumen therethrough that is coupled to an inflation fluid such as a water source 640, saline solution, and/or any other suitable inflation fluid and/or an air supply lumen that is coupled to the air source 642. In various embodiments, the fluid-supply lumen, e.g., the inflation fluid line, may be coupled to conventional inline valves (not shown) to control the flow of inflation fluid. For example, a proximal end of the inline valve may be removably coupled to a conventional inflation syringe. The fluid-supply lumen defines an inflation lumen that fluidically communicates with the interior of the conductive elastomer electrode 602 (e.g., the balloon electrode) via an aperture (not shown). The fluid-supply lumen provides a fluid communication path for inflating the conductive elastomer electrode 602 with a conductive fluid. The fluid may be either saline or air or other suitable electrically conductive inflation fluid. As previously discussed, the conductive elastomer electrode 602 is coupled to the energy source 14 to delivers electrical pulses to the esophageal cavity. The transcutaneous electrode 612 is also coupled to the energy source 14 through electrically conductive wire 608b.

In use, the electrical ablation device 600 may be introduced into a natural orifice such as the mouth 626 and advanced into a lumen, abscess, void, or cavity such as the esophagus 628, as shown in FIG. 15. In the illustrated embodiment, the conductive elastomer electrode 602 is inserted through the working channel 628 of the endoscope 622 and into the lumen or cavity defined by the esophagus 628 and the return electrode 612 is inserted transcutaneously and is located proximate to the cancerous tissue 630. Once located within the esophagus 628, the conductive elastomer electrode 602 may be inflated using either the water source 640 or the air source 642. The water source 640 may supply a conductive solution (e.g., saline solution) to enhance the conductivity of the conductive elastomer electrode 602 and to enhance the contact area between the conductive elastomer electrode 602 and the inner wall of the esophageal cavity 628 including the cancerous tissue 630. Once inflated, the conductive elastomer electrode 602 is energized by the energy source 14 with a number of high-voltage DC electrical pulses to cause necrosis of the undesirable the cancerous tissue 630 between the conductive elastomer electrode 602 and the return electrode 612. In this example, the high-voltage DC electrical pulses generate an electric field in a concentric zone around the esophageal cavity 628. The electric field has a sufficient magnitude and pulse length to induce irreversible electroporation in the undesirable cancerous tissue 630. The depth of the necrotic zone depends on the amplitude of the applied electric field, the pulse length, the number of pulses, and the repetition rate or frequency of the pulses. In various embodiments, the electrical pulses may be characterized by the parameters in accordance with the output of the energy source 14 as discussed with respect to FIGS. 1 and 5, for example.

FIGS. 17-20 illustrate a method of treating residual undesirable tissue within cavities formed in the solid tissue after removal of a mass of undesirable tissue. FIG. 17 illustrates a cross-sectional view of a breast 702 showing a cavity 700 that may be left after a lumpectomy to remove a tumor from the breast 702. In tumors that grow in solid tissue, the rate of recurrence of undesirable tissue depends on the margin of healthy tissue relative to the undesirable tissue that is removed. Accordingly, to minimize the recurrence of the tumor once the undesirable tissue is removed from the breast 702, the residual tissue in the cavity 700 should be ablated. The residual tissue may be ablated using the techniques previously described in FIGS. 13-16 above or the techniques described in FIGS. 18-20 below.

FIG. 18 illustrates one embodiment of a catheter 704 inserted into the cavity 700 left in the breast 702 after a lumpectomy procedure. A distal end 706 of the catheter 704 comprises a compressed sponge 708 or any suitable type of expandable foam material. A sleeve 710 slidably disposed over the catheter 704 and the sponge 708 contains the sponge 708 until it is ready to expand into the cavity 700. When the sleeve 710 is retracted in the direction indicated by arrow 712, the sponge 708 may be expanded into the cavity 700 by pumping saline into the sponge 708 through the catheter 704. An electrode 714 is inserted through the catheter 704 and into the sponge 708 such that the electrode 714 is in electrical communication with the sponge 708. The electrode 714 may be coupled to the positive terminal of the energy source 14, for example.

FIG. 19 illustrates an expanded sponge filling the cavity 700 left in the breast 702 following a lumpectomy as shown in FIG. 17. As shown in FIG. 19, the sponge 708 has been soaked with saline solution and has expanded to fill the cavity 700 upon removal of the sleeve 710. Multiple wire electrodes 714 may be embedded in the saline soaked sponge 708. Each of these wire electrodes 714 may be coupled to the positive terminal of the energy source 14. The body or outer portion of the breast 702 may be electrically grounded through one or more large surface area electrodes 716a,b. It will be appreciated that in other embodiments that either a single surface area electrode or more than two surface area electrodes may be employed, without limitation. The negative electrodes 716a,b are connected to the negative terminal of the energy source 14. The sponge 708 and the residual tissue within the cavity 700 are exposed to a series of electric pulses (e.g., high-voltage DC electric pulses) suitable for inducing irreversible electroporation. The high-voltage DC electric pulses in the form graphically illustrated in FIG. 5, 10, or 12 generate an electric field sufficient to cause apoptosis/necrosis in a zone extending beyond the edge of the cavity 700, for example. In various embodiments, the electrical pulses may be characterized by the parameters in accordance with the output of the energy source 14 as discussed with respect to FIGS. 1 and 5, for example.

FIG. 20 illustrates the expanded sponge 708 intact to fill the cavity 700 left in the breast 702 as shown in FIG. 17 following irreversible electroporation ablation therapy. After the irreversible electroporation ablation treatment is completed, the positive electrode 714 is removed from the cavity 700 and the negative electrodes 716a,b are removed from the breast 702. The sponge 708, however, may be left inside to fill the cavity 700.

FIG. 21 illustrates a mesh of a finite element model 709 of a sponge inserted in the cavity 700 left in the breast 702 as shown in FIG. 17. The horizontal and the vertical axes represent distance in meters (m) with the center defined at (0,0). As shown in FIG. 21, the mesh of the finite element model 709 is a two-dimensional representation of the sponge similar to the sponge 708 inserted in the cavity 700 of the breast 702 previously described in FIGS. 17-20, for example.

FIG. 22 is a graphical representation of electric potential and electrical field strength sufficient to induce irreversible electroporation when applied to the sponge 708 located within the breast cavity 700 as shown in FIG. 17. The horizontal and the vertical axes represent distance in meters (m) with the center defined at (0,0). As shown in FIG. 22, electric field strength in Volts/meter (V/m) is represented by electric field lines 718 shown as concentric contours or circles extending from an outer perimeter of the sponge 708 to a point in space 726 where the electric field strength is at a minimum. A scale 722 to the right of the graph represents electric field strength in V/m. Electric potential 720 in Volts (V) applied to the sponge 708 within the cavity 700 is represented by the shaded zones 720. A vertical scale 724 shown to the right of the electric field strength scale 722 represents electric potential in V with the minimum potential at the bottom and the maximum potential at the top. The electrical field lines 718a,b just outside the outer perimeter of the sponge 708 are representative of an electric field potential 720a of about 1400 to about 2000 V sufficient to cause cell necrosis by irreversible electroporation.

FIG. 23 is a graphical representation of electric field strength contours in volts per meter (V/m) developed when electrodes are energized by an energy source. The horizontal and the vertical axes represent distance in meters (m) with the center defined at (0,0). FIG. 23 illustrates a graph 730 of electric field strength contours developed when the electrodes 24a,b are inserted into the sponge 708 and energized by the energy source 14, as described in FIGS. 17-22. A vertical scale 732 shown to the right of the graph 730 represents the electric field strength in a range from a minimum of about 50,000V/m (bottom) to a maximum of about 100,000V/m (top). Irreversible electroporation energy in this range of electric field strength (e.g., about 50,000V/m to about 100,000V/m) are suitable for efficient and effective treatment of medical conditions that require the ablation of undesirable tissue from a localized region (i.e., in the case of the treatment of cancer). With reference to the embodiment described in FIGS. 17-22, needle-probes or electrodes 24a,b are inserted into the sponge 708. As shown in the graph 730, electric field strength contours 734, 736 represent the maximum electric field strength (e.g., about 80,000 to about 100,000V/m) in a region proximate to the location where the needle electrodes 24a,b are inserted into the sponge 708. Electric field strength contour 738 represents electric field strength of about 50,000V/m. In regions outside the sponge 708, the electric field strength peaks at contour 742 to about 100,000V/m and then tapers off with distance to about 80,000V/m at contour 744 to about 50,000V/m at contour 746. It will be appreciated that other electric field strength contours may be developed to render effective irreversible electroporation ablation therapy. Accordingly, the embodiments described herein should not be limited in this context.

The embodiments of the electrical ablation devices described herein may be introduced inside a patient using minimally invasive or open surgical techniques. In some instances it may be advantageous to introduce the electrical ablation devices inside the patient using a combination of minimally invasive and open surgical techniques. Minimally invasive techniques provide more accurate and effective access to the treatment region for diagnostic and treatment procedures. To reach internal treatment regions within the patient, the electrical ablation devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Surgical devices, such as an electrical ablation devices, may be introduced to the treatment region through the working channels of the endoscope to perform key surgical activities (KSA), including, for example, electrical ablation of tissues using irreversible electroporation energy. Some portions of the electrical ablation devices may be introduced to the tissue treatment region percutaneously or through small-keyhole-incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina). A rigid endoscope may be introduced via trocar through a relatively small-keyhole-incision (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Once an electrical ablation device is inserted in the human body internal organs may be reached using trans-organ or translumenal surgical procedures. The electrical ablation device may be advanced to the treatment site using endoscopic translumenal access techniques to perforate a lumen, and then, advance the electrical ablation device and the endoscope into the peritoneal cavity. Translumenal access procedures for perforating a lumen wall, inserting, and advancing an endoscope therethrough, and pneumoperitoneum devices for insufflating the peritoneal cavity and closing or suturing the perforated lumen wall are well known. During a translumenal access procedure, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then fed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the working channel of the endoscope.

The endoscope may be connected to a video camera (single chip or multiple chips) and may be attached to a fiber-optic cable system connected to a "cold" light source (halogen or xenon), to illuminate the operative field. The video camera provides a direct line-of-sight view of the treatment region. The abdomen is usually insufflated with carbon dioxide ($CO_2$) gas to create a working and viewing space. The abdomen is essentially blown up like a balloon (insufflated), elevating the abdominal wall above the internal organs like a dome. $CO_2$ gas is used because it is common to the human body and can be removed by the respiratory system if it is absorbed through tissue.

Once the electrical ablation devices are located at the target site, the diseased tissue may be electrically ablated or destroyed using the various embodiments of electrodes discussed herein. The placement and location of the electrodes can be important for effective and efficient electrical ablation therapy. For example, the electrodes may be positioned proximal to a treatment region (e.g., target site or worksite) either endoscopically or transcutaneously (percutaneously). In some implementations, it may be necessary to introduce the electrodes inside the patient using a combination of endoscopic, transcutaneous, and/or open techniques. The electrodes may be introduced to the tissue treatment region through a working channel of the endoscope, an overtube, or a trocar and, in some implementations, may be introduced through percutaneously or through small-keyhole-incisions.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A method for using an electrical ablation apparatus, comprising:
   inserting an elongated tubular body made of an electrically conductive material comprising an arcuate closed distal end and a first electrode received in an open proximal end of the elongated tubular body into a first natural orifice of a body, wherein the first electrode is electrically coupled to the elongated tubular body;
   inserting a second electrode, located external to the elongated tubular body, into the body;
   electrically contacting a first conductive terminal of an energy source with the first electrode, and electrically contacting a second conductive terminal of the energy source with the second electrode; and
   delivering, by the energy source, a first series of electrical pulses sufficient to induce cell necrosis by irreversible electroporation across the first electrode and the second electrode,
   wherein the first series of electrical pulses are characterized by a first amplitude, a first pulse length, and a first frequency.

2. The method of claim 1, wherein inserting an elongated tubular body into a first natural orifice of a body comprises inserting the elongated tubular body through the first natural orifice of the body into a lung of the body.

3. The method of claim 1, wherein inserting the second electrode into the body comprises inserting the second electrode into a second natural orifice of the body.

4. The method of claim 1, wherein inserting the second electrode into the body comprises inserting the second electrode transcutaneously into the body.

5. The method of claim 1, further comprising placing a distal end of the second electrode proximate to a distal end of the first electrode independent of a placement of the distal end of the first electrode.

6. An electrical ablation system, comprising:
- an elongated tubular body made of an electrically conductive material, the elongated tubular body comprising:
  - an arcuate closed distal end configured for entry into a first natural orifice of a body;
  - an open proximal end; and
  - a first electrode received in the open proximal end of the elongated tubular body, the first electrode electrically coupled to the elongated tubular body;
- a visualization device configured to visualize an internal compartment of the body and configured to receive the elongated tubular body;
- a second electrode, located external to the elongated tubular body, the second electrode configured for entry into the body; and
- an energy source having a first conductive terminal in electrical communication with the first electrode and a second conductive terminal in electrical communication with the second electrode, the energy source configured to deliver a first series of electrical pulses sufficient to induce cell necrosis by irreversible electroporation across the first electrode and the second electrode;
- wherein the first series of electrical pulses are characterized by a first amplitude, a first pulse length, and a first frequency.

7. The system of claim 6, wherein visualization device comprises an endoscope, a thoracoscope, or a laparoscope.

8. The system of claim 6, wherein visualization device comprises a plurality of working channels.

9. The system of claim 6, wherein the visualization device further comprises a viewing port.

10. The system of claim 6, wherein the second electrode further comprises a conductive portion in electrical communication with a distal end of the second electrode.

11. The system of claim 10, wherein the conductive portion is a sharpened portion.

12. The system of claim 10, wherein the conductive portion is a pad.

13. The system of claim 10, further comprising a handpiece comprising an activation switch in electrical communication with the energy source.

* * * * *